United States Patent
Dang et al.

(10) Patent No.: US 10,252,994 B2
(45) Date of Patent: Apr. 9, 2019

(54) TRANSITION METAL-CATALYZED PROTOCARBOXYLATION OF α-HALO-ACRYLIC ACID DERIVATIVES

(71) Applicant: Boehringer Ingelheim International GmbH, Ingelheim am Rhein (DE)

(72) Inventors: Mai Thi Quynh Dang, Ingelheim am Rhein (DE); Thomas Armin Hampel, Frankfurt (DE); Sandra Koch, Wiesbaden (DE); Fredrik Lars Nordstrom, Ridgefield, CT (US); Jonathan Timothy Reeves, New Milford, CT (US); Carsten Reichel, Rheinboellen (DE); Marvin Schoerer, Oberhausen (DE); Christian Stange, Ingelheim am Rhein (DE); Ivan N. Volchkov, Sandy Hook, CT (US); Li Zhong, New Milford, CT (US); Uwe Johannes Zimmermann, Trebur (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/901,921

(22) Filed: Feb. 22, 2018

(65) Prior Publication Data
US 2018/0251427 A1 Sep. 6, 2018

Related U.S. Application Data

(60) Provisional application No. 62/465,398, filed on Mar. 1, 2017, provisional application No. 62/512,777, filed on May 31, 2017.

(51) Int. Cl.
*C07D 209/48* (2006.01)
*C07C 231/12* (2006.01)

(52) U.S. Cl.
CPC .......... *C07D 209/48* (2013.01); *C07C 231/12* (2013.01)

(58) Field of Classification Search
CPC .................................................. C07D 209/48
See application file for complete search history.

(56) References Cited

PUBLICATIONS

International Search Report and Written Opinion for PCT 2018054428 dated May 7, 2018.
Chemical Abstracts Service, Columbus, Ohio, 1989, p. 1336-1340.
Chemical Abstracts Service, Columbus, Ohio, 1967, p. 1569-1571.
Goosen, Comparative Study of Copper- and Silver Catalyzed Protodecarboxylations of Carboxylic Acids, Chemcatchem, 2012, vol. 2, p. 430-442.
Rousee, Pd- and Cu-Catalyzed Stereo- and Regiocontrolled Decarboxlative/C—H Fluroalkenylation of Heteroarenes, Chem. Eur. J., vol. 20, 2014, p. 15000-150004.

*Primary Examiner* — Shawquia Jackson
(74) *Attorney, Agent, or Firm* — David L. Kershner

(57) ABSTRACT

The present invention relates to a method for the synthesis of a halo olefin of formula (I)

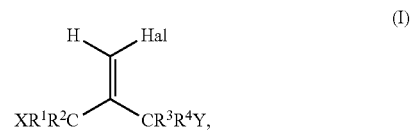

wherein Hal, $R^1$, $R^2$, $R^3$, $R^4$, X and Y are as defined herein, or a salt thereof.

13 Claims, 5 Drawing Sheets

TRANSITION METAL-CATALYZED PROTOCARBOXYLATION OF α-HALO-ACRYLIC ACID DERIVATIVES

FIELD OF THE INVENTION

The present invention relates to a method for the synthesis of a halo olefin of formula (I)

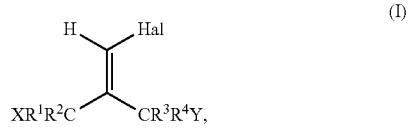

wherein the substituents Hal, $R^1$, $R^2$, $R^3$, $R^4$, X and Y are defined as hereinafter,
or a salt thereof
comprising the step of the protodecarboxylation of an α-halo-acrylic acid derivative of formula (II)

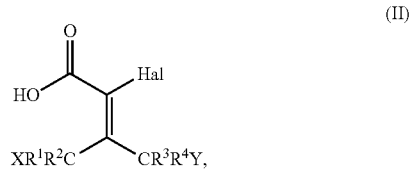

carried out in the presence of a catalytic amount of copper and/or silver.

The present invention relates also to the intermediates comprised in the method according to this invention.

BACKGROUND OF THE INVENTION

Terminal halo olefins are not only useful synthetic intermediates in organic chemistry, but also valuable target compounds themselves: There is a long-standing history of their use as monomers in polymer science (Marvel et al., *J. Am. Chem. Soc.* 1939, 61, 3241-3244), but more recently they have also attracted interest in the life sciences (e.g. Kolb et al., *J. Med. Chem.* 1987, 30, 267-272; Nunnery et al., *J. Org. Chem.* 2012, 77, 4198-4208; Akiyama et al., *Tetrahedron* 2013, 69, 6560-6564). In medicinal chemistry, for instance, terminal haloallylamine compounds have been reported to act as inhibitors of amine oxidases (WO 2005/082343, WO 2006/094201, WO 2007/120528, WO 2013/163675).

Terminal halo olefins are synthetically accessible by a limited number of approaches (van Steenis et al., *J. Chem. Soc., Perkin Trans.* 1, 2002, 2117-2133; Landelle et al., *Chem. Soc. Rev.* 2011, 40, 2867-2908; Koh et al., *Nature* 2016, 531, 459-465, Nguyen et al., *Science* 2016, 352, 569), e.g. by elimination, addition, electrophilic or nucleophilic halogenation, olefination (e.g. Wittig-type) reactions or cross-metathesis. However, the preparation of terminal halo olefins in high stereoselectivities is often one of the major challenges.

The recent approaches for the terminal halo olefin formation within the context of amine oxidase inhibitor synthesis comprise a Wittig reaction, starting from ketones, followed by separation of the E/Z isomers via chromatographic techniques or recrystallization (WO 2005/082343, WO 2007/120528, WO 2013/163675). In addition, a halogenation-dehydrohalogenation of olefins as well as the base-induced decarboxylative halogen elimination of halomethyl-substituted malonester derivatives have been disclosed (McDonald et al., *J. Med. Chem.* 1985, 28, 186-193; McDonald et al., *Tetrahedron Letters* 1985, 26, 3807-3810; WO 2005/082343, WO 2006/094201).

One further approach for the formation of terminal halo olefins is the protodecarboxylation of α-halo-acrylic acid derivatives, which are accessible, e.g. by the Horner-Wadsworth-Emmons reaction starting from carbonyl species. However, the scope of this protodecarboxylation used to be limited to particular substrates, such as perfluorated acrylic acids or acrylic acids with unsaturated β-substituents: Sodium(I), silver(I) and copper(II) salts of perfluorated acrylic acid derivatives were reported to undergo protodecarboxylation upon substantial heating (Cherstkov et al., *Izvestiya Akademii nauk SSSR, Seriya Khimicheskaya* 1986, 1, 119-122; Cherstkov et al., *Izvestiya Akademii nauk SSSR, Seriya Khimicheskaya* 1989, 6, 1336-1340). Likewise, protodecarboxylation of mucohalic acids ((Z)-2-3-dihalo-4-oxo-2-butenoic acids, i.e. bearing a carbonyl substituent in β-position) to afford (Z)-α,β-dihaloacrolein can be effected by excessive heating (Duczek et al., *Synthesis* 1992, 10, 935-936). Acrylic acid derivatives with β-pyrimidinyl-substituents may be subject to protodecarboxylation by acidification at elevated temperatures (DD 259803). Acrylic acids with β-phenyl-substituents (i.e. cinnamic acid derivatives) can be decarboxylated by employment of copper(0)/copper(II)/quinoline and heating to above 200° C. (Elkik, *Bull. Soc. Chim. Fr.* 1967, 5, 1569-71), by using excessive copper(II) in the presence of molecular sieve in DMAC/DMSO at 140° C. (Rousée et al., *Chem. Eur. J.* 2014, 20, 15000-15004) or by cofactor catalysis (Payne et al., *Nature* 2015, 522, 497-501).

In contrast, no single application of a protodecarboxylation step of acrylic acid derivatives with two vicinal saturated carbon substituents has been reported. In addition to the limited substrate scope, the use of stoichiometric amounts of metals and the heating to high temperatures constitute further drawbacks of the conversions reported to date, which have prevented a more widespread application of this reaction.

SUMMARY OF THE INVENTION

Figure 1:
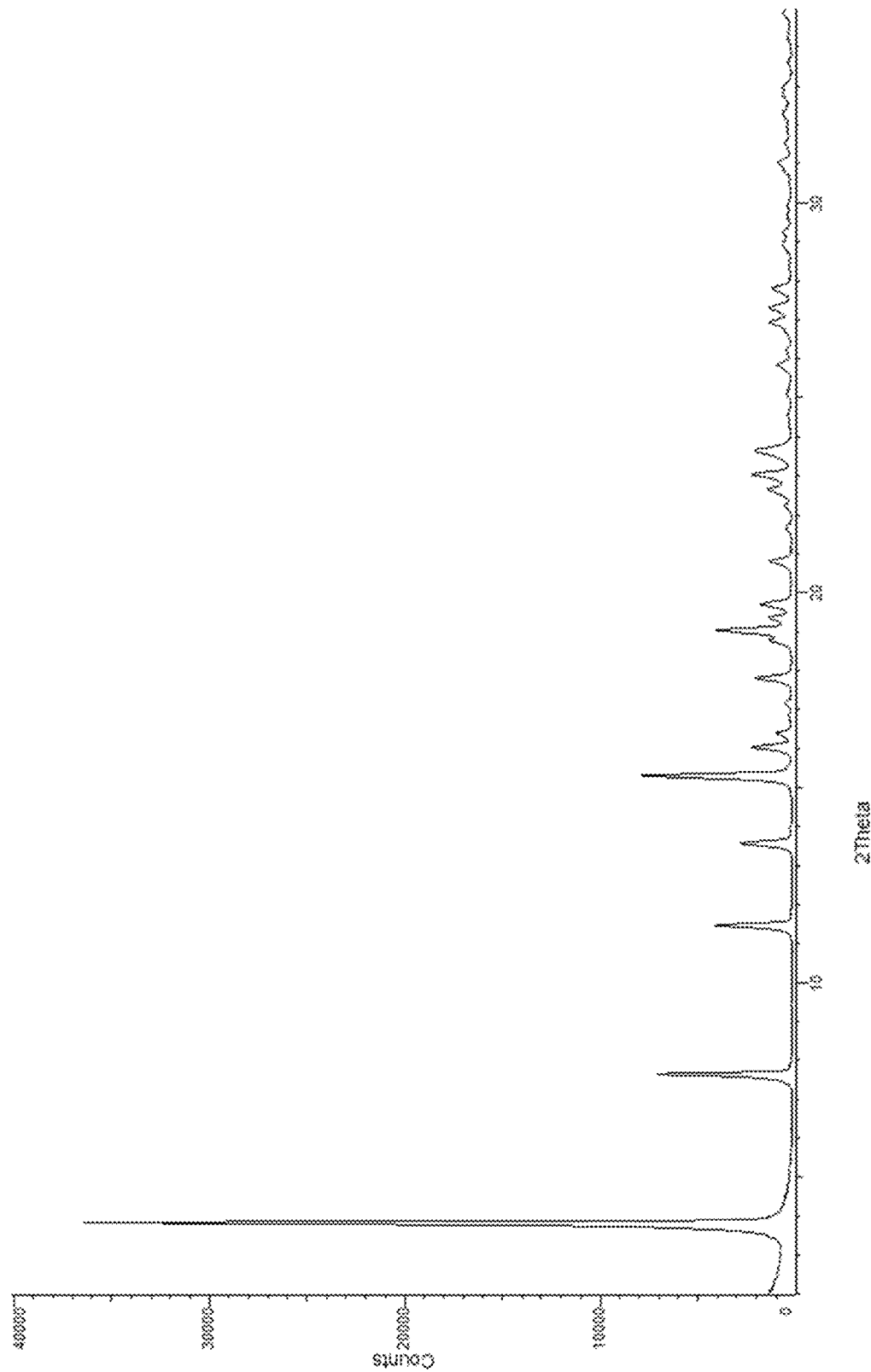
FIG. 1 shows the XRPD pattern of Form I of (I-k).

In a first aspect, the present invention relates to a method for the synthesis of a halo olefin of formula (I)

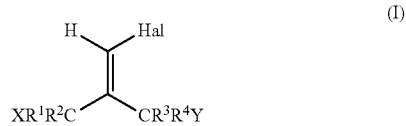

wherein
Hal is selected from the group Hal-G1 consisting of F, Cl, Br and I, and $R^1$, $R^2$, $R^3$ and $R^4$ are independently selected from the group $R^i$-G1 consisting of H, halogen, CN, substituted or unsubstituted $C_{1-10}$-alkyl, substituted or unsubstituted $C_{3-10}$-cycloalkyl, substituted or unsubstituted $C_{2-10}$-alkenyl, substituted or unsubstituted $C_{2-10}$-alkynyl, substituted or unsubstituted aryl, substituted or unsubstituted aryl-$C_{1-6}$-alkylene-, substituted or unsubstituted heteroaryl and substituted or unsubstituted heteroaryl-$C_{1-6}$-alkylene-, and X and Y are independently selected from the groups X-G1 and Y-G1, respectively, each consisting of $R^i$, $OR^X$, $SR^X$, $S(O)R^X$, $SO_2R^X$, $NR^{Y1}R^{Y2}$, $N(O)R^{Y1}R^{Y2}$, $PR^{Y1}R^{Y2}$ and $P(O)R^{Y1}R^{Y2}$, wherein $R^X$ is selected from the group $R^X$-G1 consisting of $R^i$, and wherein $R^{Y1}$ and $R^{Y2}$ are independently selected from the group $R^Y$-G1a consisting of $R^i$, $C(O)R^i$ and $C(O)OR^i$ or $R^{Y1}$ and $R^{Y2}$ are selected from the group $R^Y$-G1b in which $R^{Y1}$ and $R^{Y2}$ are linked to form, together with N or P to which they are attached, substituted or unsubstituted heteroaryl or substituted or unsubstituted heterocyclyl, and $R^i$ is selected from the group $R^i$-G1 as defined hereinbefore;

or a salt thereof comprising the step (S1)

(S1): protodecarboxylation of an α-halo-acrylic acid derivative of formula (II)

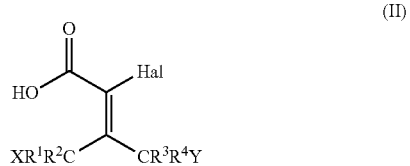

(II)

wherein Hal, $R^1$, $R^2$, $R^3$, $R^4$, X and Y are defined as hereinbefore, and wherein (S1) is carried out in the presence of a catalytic amount of copper and/or silver.

In a second aspect, the present invention relates to the intermediates that are comprised in the method according to the first aspect of the invention.

Other aspects of the present invention will become apparent to the person skilled in the art directly from the foregoing and following description.

DETAILED DESCRIPTION OF THE INVENTION

General Terms and Definitions

Unless otherwise stated, the groups, residues and substituents, particularly Hal, R, $R^0$, $R^1$, $R^2$, $R^3$, $R^4$, $R^i$, $R^X$, $R^{Y1}$, $R^{Y2}$, $R^{N1}$, $R^{N2}$, $R^{ar}$, X and Y are defined as hereinbefore and hereinafter. If groups, residues or substituents occur several times in a compound or reaction scheme, they may have the same or different meanings.

The terms "-G1", "-G2," etc., when added to the name of a residue or substituent, refer to different lists from which the particular residue or substituent may be selected.). For example, the term $R^X$-G1 denotes a first list from which $R^X$ may be selected. The elements of said lists are defined herein for each residue or substituent.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkylene-" means an aryl group which is bound to a $C_{1-3}$-alkylene-group, the latter of which is bound to the core or to the group to which the substituent is attached.

The term "$C_{1-n}$-alkyl", wherein n is an integer from 2 to n, either alone or in combination with another radical, denotes a monovalent acyclic, saturated, linear or branched hydrocarbon radical containing 1 to n C atoms. For example, the term $C_{1-4}$-alkyl includes the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—.

The term "$C_{1-n}$-alkylene" wherein n is an integer from 2 to n, either alone or in combination with another radical, denotes a divalent acyclic, saturated, linear or branched hydrocarbon radical containing 1 to n C atoms. For example, the term $C_{1-4}$-alkylene includes the radicals —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{2-n}$-alkenyl", wherein n is an integer from 3 to n, denotes a radical as defined for "$C_{1-n}$-alkyl" with at least two C atoms, wherein at least two of the carbon atoms are bonded to each other by a double bond.

The term "$C_{2-n}$-alkynyl", wherein n is an integer from 3 to n, denotes a radical as defined for "$C_{1-n}$-alkyl" with at least two C atoms, wherein at least two of the carbon atoms are bonded to each other by a triple bond.

The term "$C_{3-n}$-cycloalkyl", wherein n is an integer from 4 to n, either alone or in combination with another radical, denotes a cyclic, saturated, unbranched hydrocarbon radical containing 3 to n C atoms. For example, the term $C_{3-7}$-cycloalkyl includes cyclopropyl, cyclobutyl, cyclopentyl, cyclohexyl and cycloheptyl.

The term "aryl", either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl", either alone or in combination with another radical, denotes a saturated or unsaturated mono- or polycyclic-ring system, including aromatic ring systems, containing one or more heteroatoms selected from N, O or $S(O)_r$, wherein r=0, 1 or 2, consisting of 3 to 14 ring atoms wherein none of the heteroatoms is part of an aromatic ring. The term "heterocyclyl" is intended to include all the possible isomeric forms.

The term "heteroaryl", either alone or in combination with another radical, denotes a mono- or polycyclic ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

The term halogen generally denotes fluorine, chlorine, bromine and iodine.

The term "substituted" as used herein, means that any one or more hydrogens on the designated atom, radical or moiety are replaced by a further radical or moiety ("substituent"), provided that the atoms' normal valences are not exceeded, and that the substitution results in an acceptably stable compound. "Substituents" may be, but are not limited to halo, hydroxy, oxo, optionally halogenated alkoxy, amino, nitro, amidinyl, guanidinyl, sulfanyl, sulfo, sulfonyl, sulfonamido, silyl, optionally halogenated or hydroxylated alkyl or cycloalkyl or alkenyl, optionally halogenated or hydroxylated aryl or heteroaryl or heterocyclyl, cyano, carbonyl, acyl, alkoxycarbonyl, amido, carbamate and combinations thereof.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxy-methyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

As noted above, the present invention discloses a method for the synthesis of halo olefins comprising the step of protodecarboxylation of α-halo-acrylic acid derivatives in the presence of a catalytic amount of copper and/or silver.

In a first aspect, the present invention relates to a method for the synthesis of a halo olefin of formula (I)

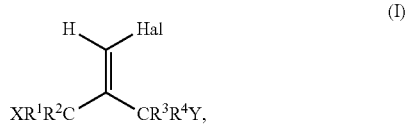

wherein Hal, $R^1$, $R^2$, $R^3$, $R^4$, X and Y are defined as hereinbefore or hereinafter,
or a salt thereof
comprising the step (S1)
(S1): protodecarboxylation of an α-halo-acrylic acid derivative of formula (II)

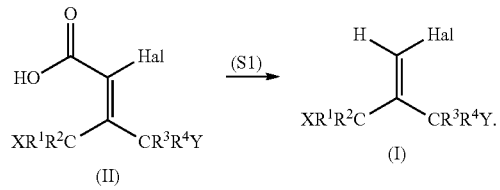

Likewise, in an analogous fashion, the invention relates to the synthesis of the E/Z isomer of (I) from the corresponding E/Z isomer of (II). In order to facilitate the following description, only the synthesis of compound (I) as depicted above will be described in detail. This is, however, not to be construed as a limitation of the scope of the invention.

In particular, the invention is to provide a process which is carried out under relatively mild and catalytic conditions.

In this aspect, it is found that the protodecarboxylation of an α-acrylic acid derivative can be effected in a stereospecific manner in the presence of catalytic amounts of the transition metals copper and/or silver.

The results of the respective investigations are presented in section Examples and Experimental Data and are summarized in the following:

For the protodecarboxylation step, best results in terms of catalytic activity, e.g. high conversions at low catalyst loadings, short reaction times and few limitations with regard to solvent selection, are obtained in the presence of silver(I). Both silver(I) oxides and salts may be employed as highly efficient catalysts, in particular silver(I) oxide, silver (I) acetate, silver(I) nitrate and silver(I) carbonate, delivering halo olefins in high yields and purities.

Good results are also obtained with copper(I), employed in the form of its oxides and/or salts, also in complexes with monodentate ligands, as catalysts for the protodecarboxylation. Non-limiting examples are copper(I) oxide, copper(I) acetate and copper(I) thiophene-2-carboxylate (CuTc).

The reaction may also proceed in the presence of copper (II).

Catalytically active copper(I) and silver(I) species may also be formed in situ from other oxidation states.

Thus, according to one embodiment of the first aspect of the present invention, the protodecarboxylation of an α-acrylic acid derivative is performed in the presence of copper and/or silver.

Preferably, copper and/or silver are employed as copper(I) oxide, copper(I) salts, silver(I) oxide and/or silver(I) salts. More preferably, silver(I) oxide or silver(I) salts are used, even more preferably silver(I) acetate and/or nitrate and/or carbonate, most preferably silver(I) acetate and/or silver(I) nitrate.

Advantageously, copper and/or silver may be employed in substoichiometric amounts in order for the protodecarboxylation to proceed rapidly to full conversion. Catalyst loadings of and below 50 mol % ("mol %" designating the amount of the catalytically active copper and/or silver atoms in relation to the molecules of the compound of formula (II)) are used very successfully. It is also found that, e.g. by adjusting the solvent volume and reaction temperature and depending on the reaction conditions, the catalyst loading may be decreased even further, at least down to the low single-digit mol % range. The actually optimum catalytic amount will of course depend on factors known to those skilled in the art such as structural features of the starting materials, further reaction conditions and parameters, acceptable reaction times and potential side reactions. Thus, according to another embodiment, copper and/or silver in the protodecarboxylation are employed in catalytic amounts, i.e. in amounts of not more than 50 mol %, e.g. in the range from 2.5 mol % to 50 mol %, preferably of not more than 20 mol %, more preferably of not more than 10 mol %, most preferably of not more than 7.5 mol %. Preferred lower limits of the catalytic range may be 7.5 mol %, 5 mol %, 2.5 mol % or 1 mol %. Most preferably, the range is from 5 mol % to 10 mol %.

The protodecarboxylation according to the present invention is advantageously carried out in dipolar aprotic solvents: For example, N-methylpyrrolidinone (NMP), N,N-dimethylacetamide (DMAC), pyridine and/or acetonitrile can be applied successfully. Working under anhydrous conditions and protection from oxygen and light are beneficial for the catalyst performance and reaction outcome.

Thus, according to another embodiment, the protodecarboxylation is carried out in a medium that comprises one or more dipolar aprotic solvents, preferably selected from the group consisting of acetonitrile, N,N-dimethylacetamide, pyridine or NMP, most preferably NMP.

The protodecarboxylation according to the present invention may be carried out without the need for excessive heating. Temperatures below 150° C. are sufficient for the reaction to proceed, most preferably in the range of 120-130° C. Full conversion can be achieved also at significantly lower temperatures, e.g. below 100° C., which may advantageously be made use of for temperature sensitive compounds unless potentially longer conversion times are unacceptable. The actually optimum reaction temperature will of course depend on factors known to those skilled in the art such as structural features of the starting materials, further reaction conditions and parameters, acceptable reaction times and potential side reactions.

Thus, according to another embodiment, the protodecarboxylation is conducted at temperatures of not more than 150° C., preferably of not more than 140° C., most preferably of not more than 130° C., e.g. at about 130° C., about 120° C., about 100° C. or about 80° C. Most preferably, the temperature range is from 120° C. to 140° C.

Optionally, step (S1) may comprise measures and steps, known to the one skilled in the art, of adding, removing or manipulating protection groups in compounds of formula (II) and/or (I). Such measures and steps may be considered necessary by the one skilled in the art depending on the meaning of the substituents, in particular X and Y, e.g. in order to avoid side reactions.

Optionally, step (S1) may comprise measures and steps, known to the one skilled in the art, of transforming the compound of formula (I) into a salt thereof, preferably into a pharmaceutically acceptable salt, most preferably into a hydrochloride salt. Such measures and steps may be considered suitable by the one skilled in the art depending on the meaning of the substituents, in particular Y, e.g. in order to improve the physical and/or chemical properties of compound (I), in particular in order to obtain the compound of formula (I) in an advantageous solid, e.g. crystalline, form that is suitable for the use in pharmaceutical development.

For instance, a preferred solid form of compound (I-k)

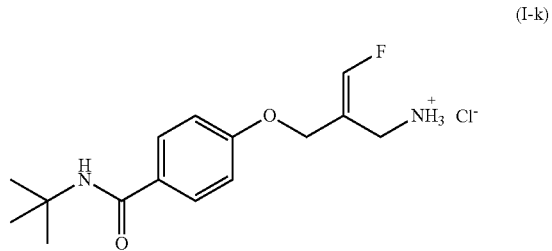 [SMILES: CC(C)(C)NC(=O)c1ccc(OC/C(=C/F)CN)cc1 ; [Cl-]]

(I-k)

is "Form I", a crystalline, high-melting, stable form of (I-k) that is not prone to polymorphic conversions. Form I is found to contain water: The molar ratio of (I-k) relative to $H_2O$ is in the range from 3:1 to 5:1, more specifically it is 4:1; Form I could therefore be considered to be a tetartohydrate.

The X-ray powder diffraction (XRPD) peaks of Form I are given in section Examples and Experimental Data. Hence, in particular, Form I is characterized by an XRPD pattern comprising peaks at 3.82, 7.63, 13.55 and 15.29 degrees 2θ, specifically comprising peaks at 3.82, 7.63, 13.55, 15.29, 16.03 and 17.80 degrees 2θ, more specifically comprising peaks at 3.82, 7.63, 11.46, 13.55, 15.29, 16.03, 17.80 and 19.02 degrees 2θ, even more specifically comprising peaks at 3.82, 7.63, 11.46, 13.55, 15.29, 16.03, 17.80, 19.02 19.69, 20.80, 22.64, 23.03, 23.63, 26.93, 27.30 and 27.79 degrees 2θ (for all peaks mentioned above: ±0.2 degrees 2θ, using CuKα1 radiation), even more specifically comprising peaks at degrees 2θ as contained in section Examples and Experimental Data (paragraph (7)) or as shown in FIG. 1 of the present application.

Figure 3:
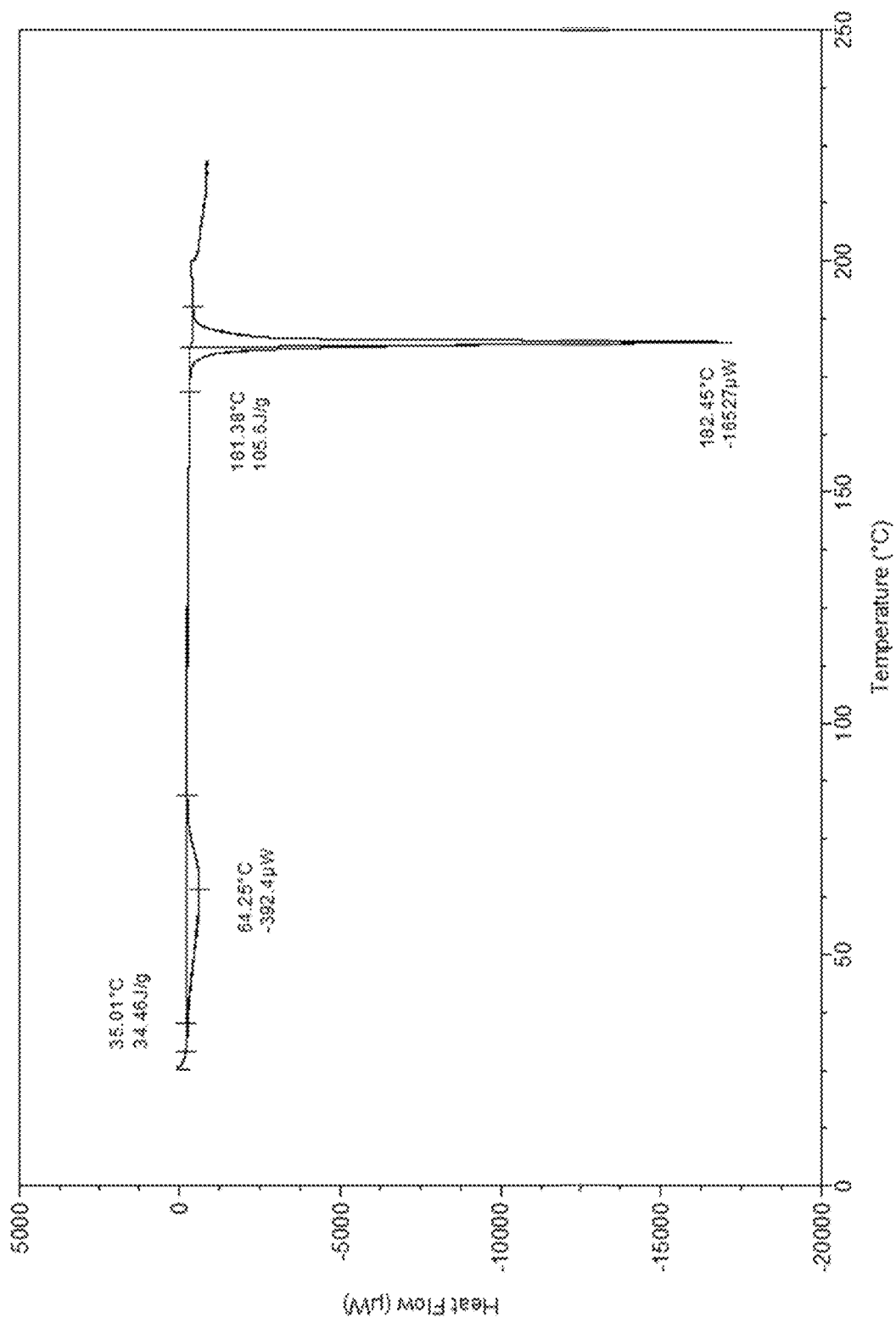
FIG. 3 shows the DSC curve of Form I of (I-k).

Form I is furthermore characterized by a melting point of about 181° C.±5° C. (determined via differential scanning calorimetry (DSC); evaluated as onset-temperature; heating rate 10° C./min). The DSC curve of Form I is depicted in FIG. 3.

Figure 4:
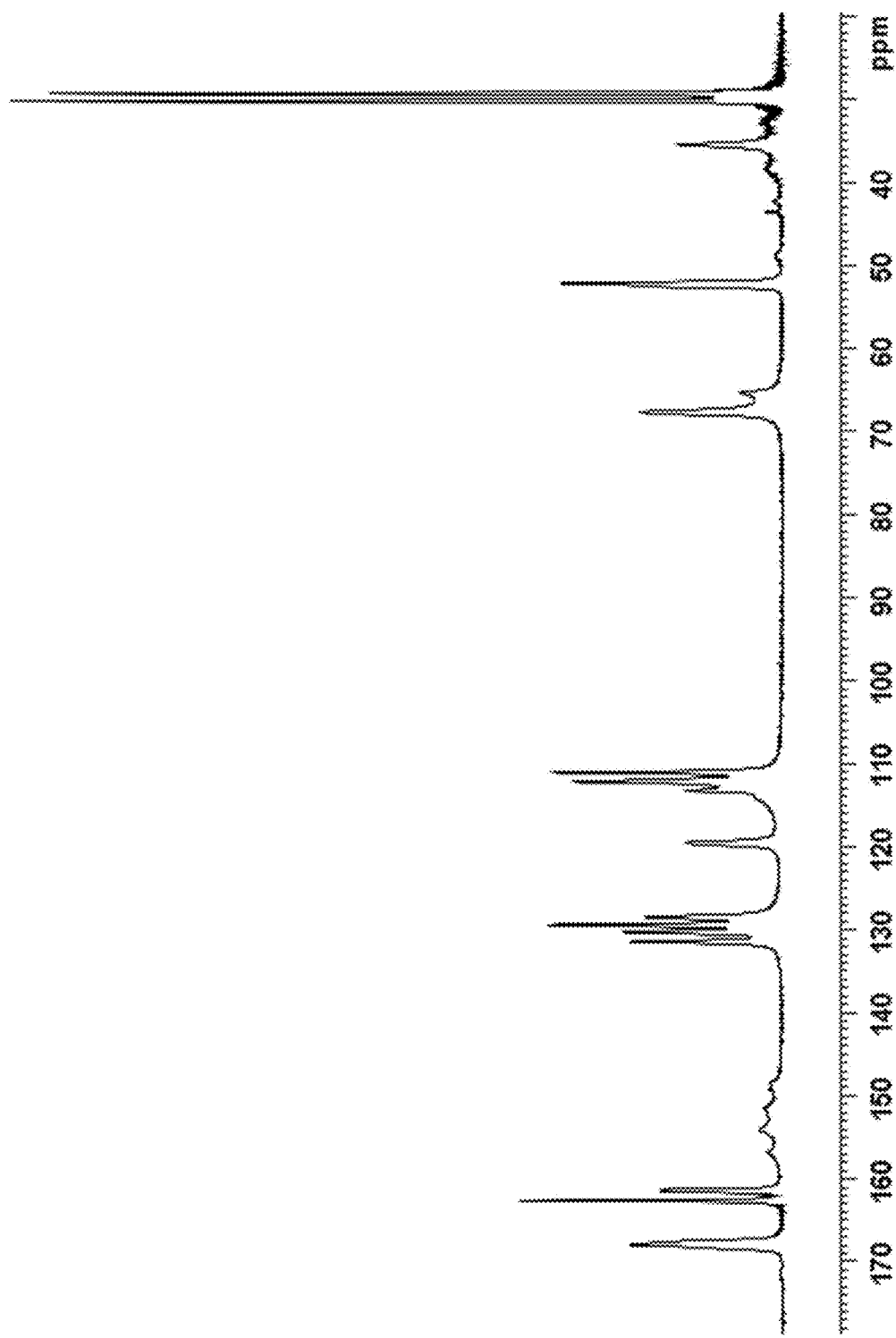
FIG. 4 shows the $^{13}$C CPMAS ssNMR spectrum of Form I of (I-k)

In addition, characteristic solid-state nuclear magnetic resonance (ssNMR) data for Form I is presented in terms of $^{13}C$ and $^{19}F$ chemical shifts in section Examples and Experimental Data. Hence, in particular, Form I is characterized by a $^{13}C$ spectrum comprising peaks at 161.1, 162.5 and 167.9 ppm, specifically comprising peaks at 148.4, 149.0, 151.4, 154.0, 156.6, 161.1, 162.5 and 167.9 ppm, more specifically comprising peaks at 128.3, 129.2, 130.1, 131.3, 148.4, 149.0, 151.4, 154.0, 156.6, 161.1, 162.5 and 167.9 ppm, even more specifically comprising peaks at 29.0, 29.9, 128.3, 129.2, 130.1, 131.3, 148.4, 149.0, 151.4, 154.0, 156.6, 161.1, 162.5 and 167.9 ppm (for all peaks mentioned above: ±0.2 ppm), even more specifically comprising peaks as contained in section Examples and Experimental Data (paragraph (9)) or as shown in FIG. 4 of the present application.

Also, Form I is characterized by a $^{19}F$ chemical shift of −115.1 ppm (±0.2 ppm).

Form I of (I-k) may be obtained from compound (I-j')

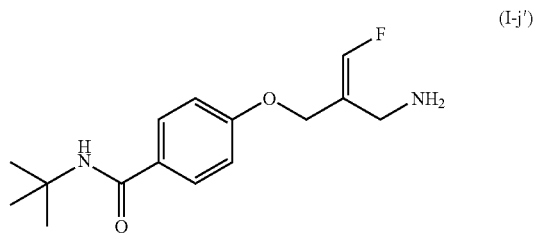 [SMILES: CC(C)(C)NC(=O)c1ccc(OC/C(=C/F)CN)cc1]

by a method comprising the following steps:
(a) addition of at least one molar equivalent of HCl to a solution of (I-j'),
(b) optionally effecting and/or supporting precipitation of (I-k),
(c) allowing crystallization of (I-k),
(d) optional isolation of the precipitate of steps (a) and/or (b) and/or (c),
(e) optional recrystallization of the precipitate of steps (a) and/or (b) and/or (c) and/or (d),
(f) isolation of Form I of (I-k).

In step (a), the mentioned solution may be prepared by dissolving (I-j') in any form obtainable, in particular in solid form, e.g. crystalline or amorphous, in a solvent or solvent mixture as described below. As an alternative, step (a) may directly adjoin the synthesis of (I-j'), i.e. without isolation or purification of (I-j'). For example, the mentioned solution may be prepared by dilution of a concentrated solution of (I-j') which was obtained by workup of the reaction mixture in which (I-j') had been formed, e.g. according to WO 2013/163675 or the present application.

Preferably the solution of (I-j') prepared in step (a) is a saturated or nearly saturated solution at the given temperature. The terms "saturated" or "nearly saturated" are related to the starting material of (I-j') as used in step (a). In particular, the concentration of (I-j') in the solution of step (a) may be in the range from about 150 mmol/L to about 600 mmol/L, e.g. about 175 mmol/L, about 270 mmol/L, about 315 mmol/L, about 370 mmol/L or about 500 mmol/L.

The solution of (I-j') used for step (a) preferably comprises at least two different solvents in order to provide both sufficient solubility for (I-j') and the desired crystallization properties for (I-k) in later steps of the process. Therefore, the medium comprises at least one protic solvent, preferably selected from alcohols, more preferably from ethanol and isopropyl alcohol, most preferably isopropyl alcohol. Also, the medium preferably comprises at least one aprotic solvent, preferably selected from alkanes, aromatic solvents, ethers and esters, more preferably from heptane, toluene, 2-methyl-tetrahydrofuran (2-Me-THF), methyl tert-butyl ether (MTBE) and ethyl acetate, most preferably from heptane, toluene and ethyl acetate.

In particular, the medium may consist of two different solvents one of which is a protic solvent. One preferred solvent mixture is isopropyl alcohol/ethyl acetate wherein the volume ratio of isopropyl alcohol and ethyl acetate is in the range from about 1:1 to 1:3, e.g. the volume ratio is about 1:2.

Also, the medium may in particular consist of three different solvents one of which is a protic solvent. One preferred solvent mixture is isopropyl alcohol/heptane/toluene wherein the volume ratio of isopropyl alcohol and heptane is in the range from about 1:1 to about 1:1.5 and wherein the volume ratio of isopropyl alcohol and toluene is in the range from about 1:3 to about 1:5, e.g. the volume ratio of the three components is about 1:1.2:3.4. Another preferred solvent mixture is isopropyl alcohol/2-Me-THF/ethyl acetate wherein the volume ratio of isopropyl alcohol and 2-Me-THF is in the range from about 1:0.3 to about 1:1 and wherein the volume ratio of isopropyl alcohol and ethyl acetate is in the range from about 1:1 to about 1:2, e.g. the volume ratio of the three components is about 1:0.5:1.2, about 1:0.4:1.3, about 1:0.6:1.5 or about 1:0.5:1.8.

The solution may be heated up to the boiling temperature of the solvent mixture or to a temperature in the range from about 65° C. to about 80° C., e.g. to about 68° C., to about 70° C. or to about 75° C. The solution may be filtered, e.g. over charcoal.

In step (a), HCl is preferably added as a solution, e.g. in isopropyl alcohol at concentrations of about 5-6 mol/L or in diethyl ether at concentrations of about 1-2 mol/L. For full conversion of (I-j') to (I-k), at least 1.0 molar equivalents (eq) of HCl are to be added, preferably from 1.0 to 1.5 eq, e.g. about 1.2 eq. The temperature during addition of HCl may be room temperature, i.e. about 20-30° C., e.g. about 25° C., or about 60-75° C., e.g. about 68° C., depending, among others, on the solvent system used.

In optional step (b), measures may be taken in order to effect and/or support the precipitation of (I-k), e.g. to facilitate nucleation. Such methods are well known to the one skilled in the art and comprise, but are not limited to the addition of seed crystals, cooling, solvent evaporation, addition of antisolvents and mechanical intervention, e.g. scratching or rubbing. Preferably, seed crystals of (I-k) are added to the solution obtained in step (a), optionally after a filtration step. The mass of the seed crystals relative to the total mass of (I-k) may be in the range up to about 5%, more preferably from about 0.001% to 1%. The seed crystals are preferably added at a temperature in the range from about 50° C. to 80° C., most preferably about 60 to 75° C., e.g. at 68° C.

In step (c), measures may be taken to allow the crystallization to proceed, preferably to completeness, e.g. to allow further crystal growth. Such methods are well known to the one skilled in the art and comprise, but are not limited to cooling, letting the suspension rest optionally while stirring, and addition of further solvents, in particular to reduce the solubility of the solute, e.g. addition of an antisolvent.

Preferably MTBE is added, e.g. about twice the total volume of isopropyl alcohol used in step (a).

Preferably, the temperature is lowered to room temperature, if applicable, in order to obtain a high yield of the precipitated form of (I-k). The duration of step (c) may be in the range from about 3 hours to about 12 hours during which stirring should preferably be applied. As known to the one skilled in the art, the size, shape and quality of the obtained crystals can be varied by the period of time and the difference of temperature in step (c).

In optional steps (d) and (e), the crystals formed in steps (b) and/or (c) may be isolated and recrystallized in order to improve the purity and quality of the crystals. The techniques used in these steps are well known to the ones skilled in the art.

Methods for isolation are detailed below for step (f).

Recrystallization according to step (e) may advantageously be performed using solvent systems that correspond to the ones described in or resulting from steps (a) to (c). Thus, the solvent system comprises at least one protic solvent and at least one aprotic solvent. Preferably the one or more protic solvents are selected from water and alcohols, more preferably from water, methanol, ethanol and isopropyl alcohol, most preferably it is isopropyl alcohol. The one or more aprotic solvents are preferably selected from alkanes, ketones, ethers and esters, more preferably from heptane, acetone, 2-methyl-tetrahydrofuran (2-Me-THF), methyl tert-butyl ether (MTBE), isopropyl acetate and ethyl acetate, most preferably from MTBE and ethyl acetate. Preferred solvent systems are selected from the group consisting of water/ethanol/ethyl acetate, water/isopropyl alcohol/ethyl acetate, isopropyl alcohol/ethyl acetate/MTBE, methanol/ethyl acetate, water/isopropyl acetate/acetone and water/isopropyl alcohol/heptane, preferably selected from water/ethanol/ethyl acetate, water/isopropyl alcohol/ethyl acetate and isopropyl alcohol/ethyl acetate/MTBE; more preferably the solvent system is isopropyl alcohol/ethyl acetate/MTBE wherein the volume ratio of isopropyl alcohol and ethyl acetate is in the range from about 1:1 to about 1:0.75 and wherein the volume ratio of isopropyl alcohol and MTBE is in the range from about 1:0.9 to about 1:0.65, e.g. the volume ratio of the three components is 9:8:7.

In step (f), Form I of (I-k) is isolated from solution by means known to the one skilled in the art which comprise, but are not limited to centrifugation and filtration. In particular, step (f) comprises filtration, washing of the filter cake and drying under vacuum. The obtained crystals are preferably washed with a solvent or a mixture of solvents, wherein the solvent is preferably selected from MTBE and a 3:1 (v/v) mixture of heptane/isopropyl alcohol followed by heptane. The most preferred solvent is MTBE. Preferably, remaining solvent(s) are advantageously removed from the crystals in a drying step under vacuum, for example at about 60° C. for about 5 to 12 hours. The temperature, the pressure and the duration of this drying step may be chosen in order to lower the content of one or more residual solvents below a given value.

Alternatively, Form I of (I-k) may be obtained from "Form II", an anhydrous form of (I-k).

Form II is obtainable by excessive drying of (I-k) or from a solution of (I-k) by evaporation of the solvent, e.g. from a solution of (I-k) in acetone upon slow evaporation of the solvent at ambient conditions or from a 50 mg/mL solution of (I-k) in methanol upon fast evaporation of the solvent, i.e. over 15 minutes at 60° C. under vacuum, preferably with dry nitrogen or dry air as vacuum oven vent gas.

Form I may be obtained from Form II by recrystallization according to techniques described herein or known to the ones skilled in the art, e.g. from water/ethanol/ethyl acetate, water/isopropyl alcohol/ethyl acetate, isopropyl alcohol/ethyl acetate/MTBE, methanol/ethyl acetate, water/isopropyl acetate/acetone and water/isopropyl alcohol/heptane, heptane, ethyl acetate, isopropyl acetate, isopropyl alcohol, anisole, methyl ethyl ketone, α,α,α-trifluoro toluene and mixtures thereof, preferably from heptane, ethyl acetate, isopropyl acetate, anisole, ethyl acetate/isopropyl alcohol 1:1 and α,α,α-trifluoro toluene/methyl ethyl ketone 1:1. In addition, the recrystallization procedure as disclosed above in step (e) may be employed.

Also, Form I may be obtained by reconditioning of Form II, i.e. by exposing Form II to relative humidities of not less than 15%.

Differentiation between Form I and Form II and hence monitoring of the completeness of the conversion may be achieved by collecting X-ray powder diffraction (XRPD) and/or differential scanning calorimetry (DSC) and/or solid-state nuclear magnetic resonance (ssNMR) data as far as they are characteristic for the different crystalline forms.

As a further alternative, Form I of (I-k) may be formed from ethanol solvates of (I-k).

Ethanol solvates of (I-k), in particular in a 1:1 molar ratio, can be recovered from ethanol and ethanol/heptane solvent systems, e.g. of volume ratios of ethanol:heptane of 2:1, 1:1, and 1:2, preferably from ethanol or ethanol/heptane 1:1, upon evaporation at room temperature.

Form I may be obtained from ethanol solvates by recrystallization according to techniques described herein or known to the ones skilled in the art, e.g. from water/ethanol/ethyl acetate, water/isopropyl alcohol/ethyl acetate, isopropyl alcohol/ethyl acetate/MTBE, methanol/ethyl acetate, water/isopropyl acetate/acetone and water/isopropyl alcohol/heptane, heptane, ethyl acetate, isopropyl acetate, isopropyl alcohol, anisole, methyl ethyl ketone, α,α,α-trifluoro toluene and mixtures thereof, preferably from heptane, ethyl acetate, isopropyl acetate, anisole, ethyl acetate/isopropyl alcohol 1:1 and α,α,α-trifluoro toluene/methyl ethyl ketone 1:1. In addition, the recrystallization procedure as disclosed above in step (e) may be employed.

Also, Form I may be obtained from ethanol solvates of (I-k) by desolvation upon drying at ambient conditions or heating to temperatures in the range from about 75° C. to about 110° C.

The present invention also provides a method for the synthesis of a halo olefin of formula (I)

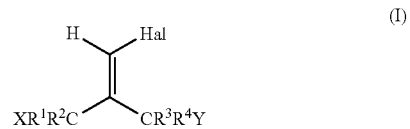

wherein Hal, $R^1$, $R^2$, $R^3$, $R^4$, X and Y are defined as hereinbefore or hereinafter comprising the steps (S2): formation of an α-halo-acrylic acid derivative of formula (II) from ketone (III) and (S1) as defined hereinbefore or hereinafter

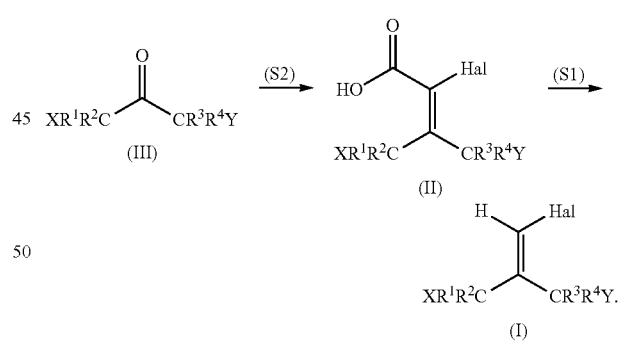

In particular, a method for the stereoselective conversion from a ketone of formula (III) to a halo olefin of formula (I) is provided.

Previous approaches for the terminal halo olefin (I) formation from ketones (III) have typically proceeded via Wittig reactions which often deliver poor E/Z selectivities and therefore necessitate further potentially cumbersome separation steps and impact the overall reaction yield (van Steenis et al., *J. Chem. Soc., Perkin Trans.* 1, 2002, 2117-2133; Landelle et al., *Chem. Soc. Rev.* 2011, 40, 2867-2908).

The protodecarboxylation (S1) of the present invention, in contrast, paves the way for said conversion from (III) to (I) to be performed via α-halo-acrylic acid derivatives of formula (II). Compounds of formula (II) are readily accessible from ketones (III) by the Horner-Wadsworth-Emmons reaction which may, with the proper choice of the base, deliver improved E/Z selectivities in comparison to Wittig olefinations. This improved selectivity is maintained in the stereo-specific protodecarboxylation of (II) to form olefin (I). Overall, the incorporation of the protodecarboxylation into said conversion from (III) to (I) thus allows for obtaining improved E/Z selectivities, installed in the formation of (II) (step (S2)) and maintained in its protodecarboxylation (step (S1)). This more favorable isomeric purity in turn may help to simplify or avoid further isomeric separation e.g. by crystallization or chromatography, and to improve the reaction yield. Also, in this reaction sequence, the option is provided to perform isomeric separation—additionally or only—on the stage of the intermediate (II), which, depending on the particular circumstances, may be more effective and/or efficient than on the stage of the product (I).

Step (S2) is explained in more detail in the following:

The α-halo-acrylic acid derivative of formula (II') can in principle be formed from ketones (III) via Horner-Wadsworth-Emmons protocols known in the art (e.g. Maryanoff et al., *Chem. Rev.* 1989, 89, 863-927; Al Jasem et al., *J. Chem. Res.* 2014, 38, 453-463; Sano et al., *Tetrahedron Letters* 2014, 55, 6248-6251), e.g. by using phosphonates of formula (IV) as reagents in the presence of basic additives:

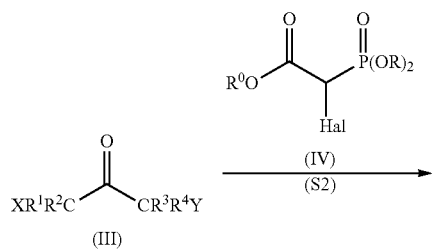

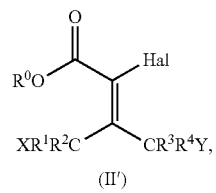

wherein Hal, R, $R^0$, $R^1$, $R^2$, $R^3$, $R^4$, X and Y are defined as hereinbefore or hereinafter.

In case $R^0$ is not H, (S2) preferably also comprises the saponification of the acrylic acid ester (II') to the acrylic acid (II), for instance saponification in situ, according to procedures known to the one skilled in the art.

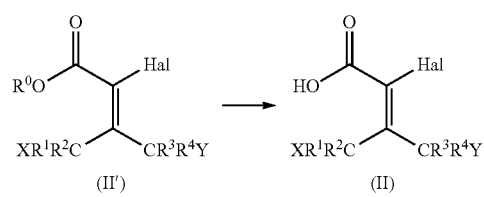

The saponification may be performed either prior to or after separation and/or isolation of the E/Z isomers. The formation of the acrylic acid by saponification may also be beneficial for the separation of the E and Z isomers either by chromatographic methods or by crystallization.

An example of a synthesis according to the step (S2) is:

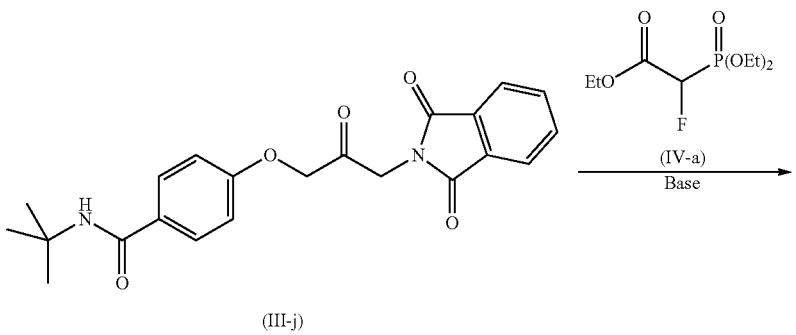

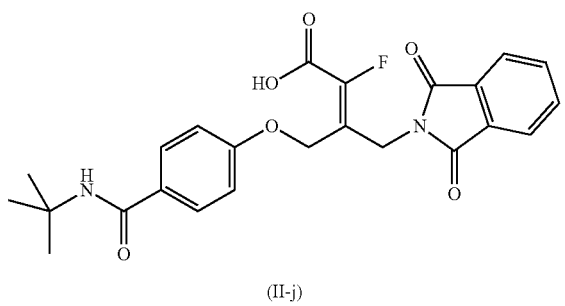

It is found for the conversion of (III) to (II) in the presence of (IV), in particular from (III-j) to (II-j) in the presence of (IV-a), that good to very good reaction yields can be obtained with a number of different bases, e.g. n-BuLi, NaHMDS, NaH, t-BuONa, t-BuOK, (t-BuO)$_2$Mg and n-Bu$_2$Mg. However, best results in terms of E/Z ratio of the product are observed when organomagnesium halides, such as MeMgCl, MeMgBr, MeMgI, EtMgBr and i-PrMgCl, are used as bases. Preferably, organomagnesium bromides or iodides, such as MeMgBr, MeMgI and EtMgBr, are used.

Thus, according to one embodiment, the method for the synthesis of a halo olefin of formula (I) comprises the steps (S2) and (S1):

(S2): reacting a ketone of formula (III) with a phosphonate of formula (IV) in the presence of at least one basic additive, preferably an organomagnesium halide, more preferably C$_{1-4}$-alkyl magnesium chloride or C$_{1-4}$-alkyl magnesium bromide, for example MeMgBr, MeMgCl, EtMgBr or i-PrMgCl, most preferably EtMgBr; and saponification of the acrylic acid ester of formula (II') (in case R$^0$ is not H), and (S1): the protodecarboxylation of the α-halo-acrylic acid derivative of formula (II), carried out in the presence of a catalytic amount of copper and/or silver.

In addition, (S2) may optionally comprise measures and steps, known to the one skilled in the art, for the separation of the E and Z isomers to improve the purity of the product, for example, chromatographic methods or crystallization. For instance, the E/Z separation may be performed by crystallization of compound (II), e.g. after the saponification of (II') to (II).

Thus, according to another embodiment,
(S2) additionally comprises the E/Z purification of the compound of formula (II).

According to another embodiment, the halo olefin of formula (I) is formed from ketone (III) with an E/Z selectivity of not less than 80:20, preferably not less than 90:10, most preferably not less than 95:5 via the steps (S2), comprising saponification in case R$^0$ is not H and optionally comprising E/Z purification, and (S1).

According to another embodiment, (S2) is carried out at temperatures in the range from −20° C. to 70° C., preferably in the range from −10° C. to 40° C.

According to another embodiment, (S2) is carried out in an aprotic medium, preferably selected from the group consisting of tetrahydrofuran (THF), 2-methyl-THF, dimethylsulfoxide (DMSO), dimethylether (DME), toluene (PhMe) and mixtures thereof, preferably in THF, 2-methyl-THF and mixtures thereof.

According to another embodiment, the compound of formula (IV) in (S2) is employed in amounts of 1 to 2.5 equivalents in relation to compound (III), preferably in an amount of 1.1 to 1.5 equivalents, most preferably in an amount of about 1.2 equivalents.

Optionally, step (S2) may comprise measures and steps, known to the one skilled in the art, of adding, removing or manipulating protection groups in compounds of formula (III) and/or (II). Such measures and steps may be considered necessary by the one skilled in the art depending on the meaning of the substituents, in particular X and Y, e.g. in order to avoid side reactions.

In the processes according to this invention, the following meanings of groups, residues and substituents are preferred. Any and each of the above and below definitions of the groups, residues and substituents may be combined with each other:

According to one embodiment,
Hal is selected from the group Hal-G1 consisting of F, Cl, Br and I.

According to another embodiment,
Hal is selected from the group Hal-G2 consisting of F and Cl.

According to another embodiment,
Hal is selected from the group Hal-G3 consisting of F.

According to another embodiment,
R$^1$, R$^2$, R$^3$ and R$^4$ are independently selected from the group R$^i$-G1 consisting of
H, halogen, CN, substituted or unsubstituted C$_{1-10}$-alkyl, substituted or unsubstituted C$_{3-10}$-cycloalkyl, substituted or unsubstituted C$_{2-10}$-alkenyl, substituted or unsubstituted C$_{2-10}$-alkynyl, substituted or unsubstituted aryl, substituted or unsubstituted aryl-C$_{1-6}$-alkylene-, substituted or unsubstituted heteroaryl and substituted or unsubstituted heteroaryl-C$_{1-6}$-alkylene-.

According to another embodiment,
R$^1$, R$^2$, R$^3$ and R$^4$ are independently selected from the group R$^i$-G2 consisting of
H, halogen, CN, methyl, ethyl, n-propyl, iso-propyl, n-butyl, sec-butyl, iso-butyl, tert-butyl and cyclopropyl, wherein said methyl, ethyl, n-propyl, iso-propyl, n-butyl, sec-butyl, iso-butyl, tert-butyl and cyclopropyl may be partially or fully halogenated, preferably fluorinated.

According to another embodiment,
R$^1$, R$^2$, R$^3$ and R$^4$ are independently selected from the group R$^i$-G3 consisting of
H, halogen, CN and methyl, wherein said methyl may be partially or fully halogenated, preferably fluorinated.

According to another embodiment,
R$^1$, R$^2$, R$^3$ and R$^4$ are independently selected from the group R$^i$-G4 consisting of H.

According to another embodiment,
X is selected from the group X-G1 consisting of
R$^i$, OR$^X$, SR$^X$, S(O)R$^X$, SO$_2$R$^X$, NR$^{Y1}$R$^{Y2}$, N(O)R$^{Y1}$R$^{Y2}$, PR$^{Y1}$R$^{Y2}$ and P(O)R$^{Y1}$R$^{Y2}$,
wherein R$^i$, R$^X$, R$^{Y1}$ and R$^{Y2}$ are defined as hereinbefore or hereinafter.

According to another embodiment,
X is selected from the group X-G2 consisting of
OR$^X$, SR$^X$, S(O)R$^X$ and SO$_2$R$^X$,
wherein R$^X$ is defined as hereinbefore or hereinafter.

According to another embodiment,
X is selected from the group X-G3 consisting of
OR$^X$,
wherein R$^X$ is defined as hereinbefore or hereinafter.

According to another embodiment,
R$^i$ is selected from the group R$^i$-G1 as defined hereinbefore.

According to another embodiment,
R$^i$ is selected from the group R$^i$-G2 as defined hereinbefore.

According to another embodiment,
R$^i$ is selected from the group R$^i$-G3 as defined hereinbefore.

According to another embodiment,
R$^i$ is selected from the group R$^i$-G4 as defined hereinbefore.

According to another embodiment,
R$^X$ is selected from the group R$^X$-G1 consisting of
R$^i$ as defined hereinbefore or hereinafter.

According to another embodiment,
R$^X$ is selected from the group R$^X$-G2 consisting of
H, substituted or unsubstituted C$_{1-10}$-alkyl, substituted or unsubstituted C$_{3-10}$-cycloalkyl, substituted or unsubstituted C$_{2-10}$-alkenyl, substituted or unsubstituted C$_{2-10}$-alkynyl, substituted or unsubstituted aryl, substituted or unsubstituted aryl-$C_{1-6}$-alkylene-, substituted or unsubstituted heteroaryl and substituted or unsubstituted heteroaryl-$C_{1-6}$-alkylene-.

According to another embodiment,
$R^X$ is selected from the group $R^X$-G3 consisting of aryl and heteroaryl, all of which substituted with $R^{ar}$, wherein $R^{ar}$ is defined as hereinbefore or hereinafter.

According to another embodiment,
$R^X$ is selected from the group $R^X$-G4 consisting of phenyl, substituted with $R^{ar}$ wherein $R^{ar}$ is defined as hereinbefore or hereinafter.

According to another embodiment,
$R^{ar}$ is selected from the group $R^{ar}$-G1 consisting of $C(O)NR^{N1}R^{N2}$ and $SO_2NR^{N1}R^{N2}$,
wherein $R^{N1}$ and $R^{N2}$ are defined as hereinbefore or hereinafter.

According to another embodiment,
$R^{ar}$ is selected from the group $R^{ar}$-G2 consisting of $C(O)NR^{N1}R^{N2}$,
wherein $R^{N1}$ and $R^{N2}$ are defined as hereinbefore or hereinafter.

According to another embodiment,
$R^{ar}$ is selected from the group $R^{ar}$-G3 consisting of $C(O)NHt$-Bu.

According to another embodiment,
$R^{N1}$ and $R^{N2}$ are independently selected from the group $R^N$-G1 consisting of
H, substituted or unsubstituted $C_{1-6}$-alkyl and substituted or unsubstituted $C_{3-7}$-cycloalkyl.

According to another embodiment,
$R^{N1}$ and $R^{N2}$ are independently selected from the group $R^N$-G2 consisting of
H and substituted or unsubstituted methyl, ethyl, n-propyl, iso-propyl, n-butyl, sec-butyl, iso-butyl and tert-butyl.

According to another embodiment,
$R^{N1}$ and $R^{N2}$ are independently selected from the group $R^N$-G3 consisting of
H and tert-butyl.

According to another embodiment,
Y is selected from the group Y-G1 consisting of
$R^i$, $OR^X$, $SR^X$, $S(O)R^X$, $SO_2R^X$, $NR^{Y1}R^{Y2}$, $N(O)R^{Y1}R^{Y2}$, $PR^{Y1}R^{Y2}$ and $P(O)R^{Y1}R^{Y2}$,
wherein $R^i$, $R^X$, $R^{Y1}$ and $R^{Y2}$ are defined as hereinbefore or hereinafter.

According to another embodiment,
Y is selected from the group Y-G2 consisting of
$NR^{Y1}R^{Y2}$, $PR^{Y1}R^{Y2}$ and $P(O)R^{Y1}R^{Y2}$,
wherein $R^{Y1}$ and $R^{Y2}$ are defined as hereinbefore or hereinafter.

According to another embodiment,
Y is selected from the group Y-G3 consisting of
$NR^{Y1}R^{Y2}$,
wherein $R^{Y1}$ and $R^{Y2}$ are defined as hereinbefore or hereinafter.

According to another embodiment,
Y is selected from the group Y-G4 consisting of
$NR^{Y1}R^{Y2}$,
wherein $R^{Y1}$ and $R^{Y2}$ are defined as hereinbefore or hereinafter.

According to another embodiment,
$R^{Y1}$ and $R^{Y2}$ are independently selected from the group $R^Y$-G1a consisting of
$R^i$, $C(O)R^i$ and $C(O)OR^i$, wherein $R^i$ is defined as hereinbefore, or
$R^{Y1}$ and $R^{Y2}$ are selected from the group $R^Y$-G1b in which $R^{Y1}$ and $R^{Y2}$ are linked to form, together with N or P to which they are attached, substituted or unsubstituted heteroaryl or substituted or unsubstituted heterocyclyl.

According to another embodiment,
$R^{Y1}$ and $R^{Y2}$ are independently selected from the group $R^Y$-G2a consisting of
H, substituted or unsubstituted $C_{1-10}$-alkyl, substituted or unsubstituted $C_{3-10}$-cycloalkyl, substituted or unsubstituted $C_{2-10}$-alkenyl, substituted or unsubstituted aryl, substituted or unsubstituted aryl-$C_{1-6}$-alkylene-, substituted or unsubstituted $C_{1-10}$-alkyl-$C(O)$—, substituted or unsubstituted aryl-$C(O)$—, substituted or unsubstituted aryl-$C_{1-6}$-alkylene-$C(O)$—, substituted or unsubstituted $C_{1-10}$-alkyl-$OC(O)$—, substituted or unsubstituted aryl-$OC(O)$— and substituted or unsubstituted aryl-$C_{1-6}$-alkylene-$OC(O)$— or
$R^{Y1}$ and $R^{Y2}$ are selected from the group $R^Y$-G2b in which $R^{Y1}$ and $R^{Y2}$ are linked to form, together with N or P to which they are attached, substituted or unsubstituted heteroaryl or substituted or unsubstituted heterocyclyl.

According to another embodiment,
$R^{Y1}$ and $R^{Y2}$ are independently selected from the group $R^Y$-G3a consisting of
H, substituted or unsubstituted $C_{1-6}$-alkyl, substituted or unsubstituted $C_{2-6}$-alkenyl, substituted or unsubstituted aryl, substituted or unsubstituted aryl-$C_{1-4}$-alkylene-, substituted or unsubstituted $C_{1-6}$-alkyl-$C(O)$—, substituted or unsubstituted aryl-$C(O)$—, substituted or unsubstituted aryl-$C_{1-4}$-alkylene-$C(O)$—, substituted or unsubstituted $C_{1-6}$-alkyl-$OC(O)$—, substituted or unsubstituted aryl-$OC(O)$— and substituted or unsubstituted aryl-$C_{1-4}$-alkylene-$OC(O)$— or
$R^{Y1}$ and $R^{Y2}$ are selected from the group $R^Y$-G3b in which $R^{Y1}$ and $R^{Y2}$ are linked to form, together with N or P to which they are attached, substituted or unsubstituted heteroaryl or substituted or unsubstituted heterocyclyl.

According to another embodiment,
$R^{Y1}$ and $R^{Y2}$ are independently selected from the group $R^Y$-G4a consisting of
H, substituted or unsubstituted Ac (acetyl), substituted or unsubstituted Boc (tert-butyloxycarbonyl), substituted or unsubstituted Cbz (carboxybenzyl), substituted or unsubstituted Fmoc (fluorenylmethyloxycarbonyl), substituted or unsubstituted Alloc (allyloxycarbonyl), substituted or unsubstituted t-Bu (tert-butyl), substituted or unsubstituted Bn (benzyl) and substituted or unsubstituted phthaloyl or
$R^{Y1}$ and $R^{Y2}$ are selected from the group $R^Y$-G4b in which $R^{Y1}$ and $R^{Y2}$ are linked to form, together with N to which they are attached, substituted or unsubstituted phthalimide or substituted or unsubstituted pyrrole.

According to another embodiment,
$R^{Y1}$ and $R^{Y2}$ are independently selected from the group $R^Y$-G5a consisting of
H and substituted or unsubstituted phthaloyl or
$R^{Y1}$ and $R^{Y2}$ are selected from the group $R^Y$-G5b in which $R^{Y1}$ and $R^{Y2}$ are linked to form, together with N to which they are attached, substituted or unsubstituted phthalimide.

According to another embodiment,
$R^{Y1}$ and $R^{Y2}$ are independently selected from the group $R^Y$-G6 consisting of H.

Further subgeneric embodiments of the compounds of formula (I) are set forth as embodiments (I-a) to (I-f) in the following table, wherein the above-mentioned substituent definitions are used ($R^1$, $R^2$, $R^3$ and $R^4$ as well as $R^{N1}$ and $R^{N2}$ are meant to be selected independently from the given group; $R^{Y1}$ and $R^{Y2}$ are meant to be selected independently from the given subgroup designated with "a" or selected from the given subgroup designated with "b"):

| Embodiment | Hal | $R^1, R^2$ $R^3, R^4$ | X | $R^X$ | $R^{ar}$ | $R^{N1}, R^{N2}$ | Y | $R^{Y1}, R^{Y2}$ |
|---|---|---|---|---|---|---|---|---|
| (I-a) | Hal-G2 | $R^i$-G2 | X-G2 | $R^X$-G2 | $R^{ar}$-G1 | $R^N$-G1 | Y-G3 | $R^Y$-G4a or $R^Y$-G4b |
| (I-b) | Hal-G2 | $R^i$-G3 | X-G3 | $R^X$-G3 | $R^{ar}$-G1 | $R^N$-G2 | Y-G4 | $R^Y$-G4a or $R^Y$-G4b |
| (I-c) | Hal-G2 | $R^i$-G3 | X-G3 | $R^x$-G4 | $R^{ar}$-G1 | $R^N$-G2 | Y-G4 | $R^Y$-G4a or $R^Y$-G4b |
| (I-d) | Hal-G2 | $R^i$-G3 | X-G3 | $R^X$-G4 | $R^{ar}$-G2 | $R^N$-G2 | Y-G4 | $R^Y$-G5a or $R^Y$-G5b |
| (I-e) | Hal-G3 | $R^i$-G3 | X-G3 | $R^X$-G4 | $R^{ar}$-G2 | $R^N$-G2 | Y-G4 | $R^Y$-G5a or $R^Y$-G5b |
| (I-f) | Hal-G3 | $R^i$-G4 | X-G3 | $R^X$-G4 | $R^{ar}$-G2 | $R^N$-G2 | Y-G4 | $R^Y$-G5a or $R^Y$-G5b |

According to one embodiment,
in step (S1), the compound of formula (II) is compound (II-g)

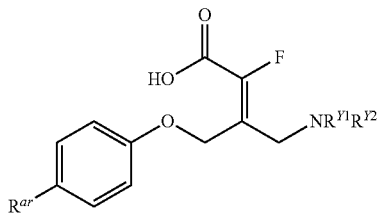

(II-g)

wherein $R^{ar}$ as well as $R^{Y1}$ and $R^{Y2}$ are defined as hereinbefore or hereinafter,
preferably $R^{ar}$ is selected from the group $R^{ar}$-G1 as defined hereinbefore, more preferably from the group $R^{ar}$-G2 as defined hereinbefore, wherein
$R^{N1}$ and $R^{N2}$ are preferably independently selected from the group $R^N$-G2 as defined hereinbefore, more preferably from the group $R^N$-G3 as defined hereinbefore, and
preferably $R^{Y1}$ and $R^{Y2}$ are independently selected from the group $R^Y$-G4a as defined hereinbefore or are selected from the group $R^Y$-G4b as defined hereinbefore, more preferably independently selected from the group $R^Y$-G5a as defined hereinbefore or are selected from the group $R^Y$-G5b as defined hereinbefore,
and the compound of formula (I) is compound (I-g)

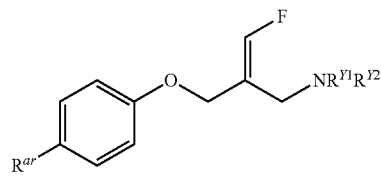

(I-g)

wherein $R^{ar}$ as well as $R^{Y1}$ and $R^{Y2}$ are defined as hereinbefore.
According to another embodiment,
in step (S1), the compound of formula (II) is compound (II-h)

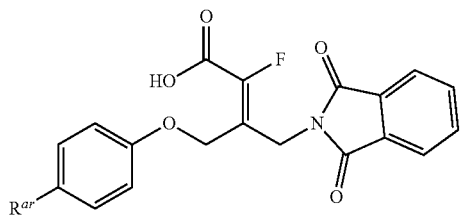

(II-h)

wherein $R^{ar}$ is selected from the group $R^{ar}$-G2 as defined hereinbefore in connection with $R^N$-G2 as defined hereinbefore,
and the compound of formula (I) is compound (I-h)

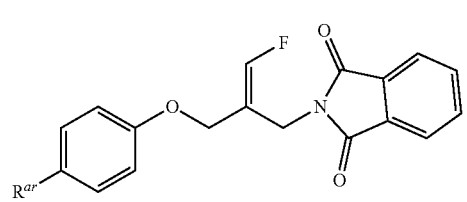

(I-h)

wherein $R^{ar}$ is defined as hereinbefore.
According to another embodiment,
in step (S1), the compound of formula (II) is compound (II-i)

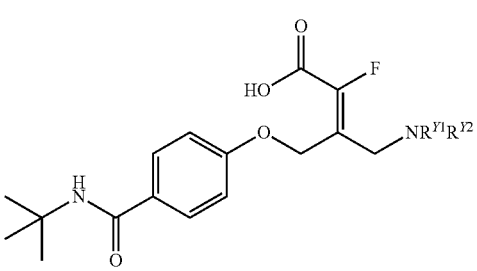

(II-i)

wherein $R^{Y1}$ and $R^{Y2}$ are independently selected from the group $R^Y$-G4a as defined hereinbefore or are selected from the group $R^Y$-G4b as defined hereinbefore, and the compound of formula (I) is compound (I-i)

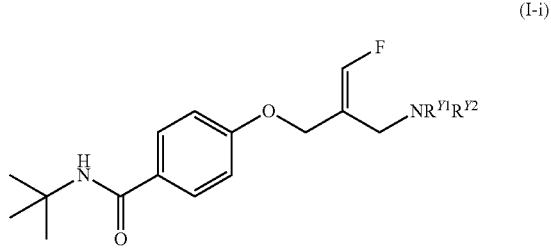

(I-i)

wherein $R^{Y1}$ and $R^{Y2}$ are defined as hereinbefore.

According to another embodiment, in step (S1), the compound of formula (II) is compound (II-j)

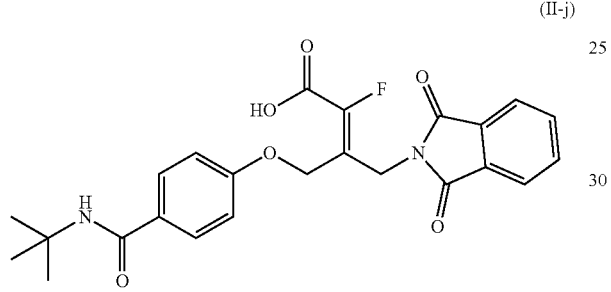

(II-j)

and the compound of formula (I) is compound (I-j)

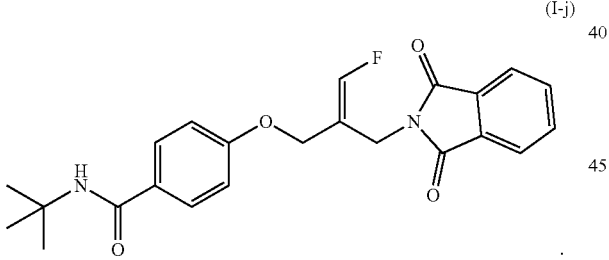

(I-j)

According to one embodiment, step (S1) comprises the deprotection of compound (I-g)

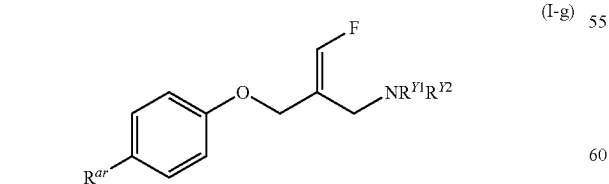

(I-g)

wherein $R^{ar}$ as well as $R^{Y1}$ and $R^{Y2}$ are defined as hereinbefore or hereinafter, preferably $R^{ar}$ is selected from the group $R^{ar}$-G1 as defined hereinbefore, more preferably from the group $R^{ar}$-G2 as defined hereinbefore, wherein $R^{N1}$ and $R^{N2}$ are preferably independently selected from the group $R^N$-G2 as defined hereinbefore, more preferably from the group $R^N$-G3 as defined hereinbefore, and preferably $R^{Y1}$ and $R^{Y2}$ are independently selected from the group $R^Y$-G4a as defined hereinbefore or are selected from the group $R^Y$-G4b as defined hereinbefore, more preferably independently selected from the group $R^Y$-G5a as defined hereinbefore or are selected from the group $R^Y$-G5b as defined hereinbefore, to compound (I-g')

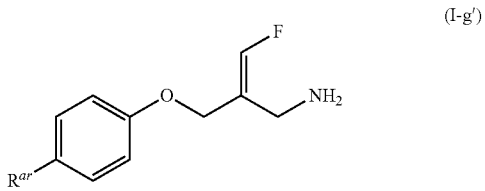

(I-g')

wherein $R^{ar}$ is defined as hereinbefore.

According to another embodiment, step (S1) comprises the deprotection of compound (I-h)

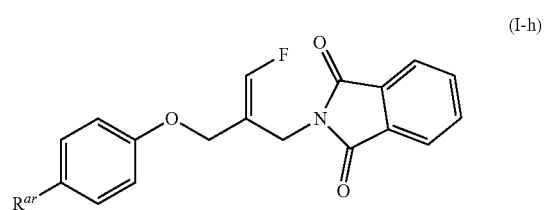

(I-h)

wherein $R^{ar}$ is selected from the group $R^{ar}$-G2 as defined hereinbefore in connection with $R^N$-G2 as defined hereinbefore, to compound (I-h')

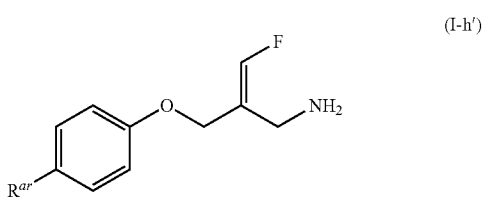

(I-h')

wherein $R^{ar}$ is defined as hereinbefore.

According to another embodiment, step (S1) comprises the deprotection of compound (I-i)

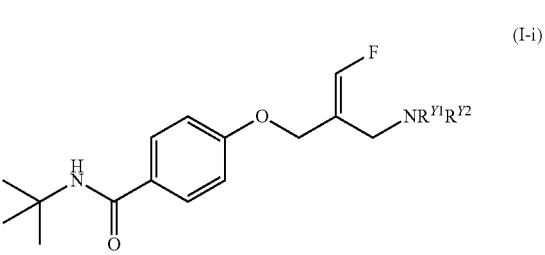

(I-i)

wherein $R^{Y1}$ and $R^{Y2}$ are independently selected from the group $R^Y$-G4a as defined hereinbefore or are selected from the group $R^Y$-G4b as defined hereinbefore, to compound (I-j')

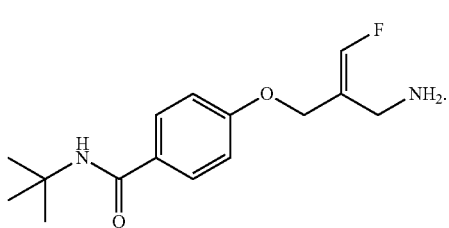

According to another embodiment,
step (S1) comprises the deprotection of compound (I-j)

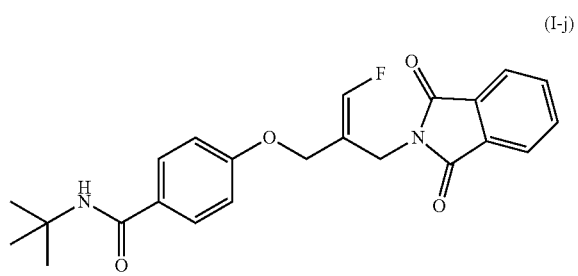 [SMILES: CC(C)(C)NC(=O)c1ccc(OC/C(=C/F)CN2C(=O)c3ccccc3C2=O)cc1]

to compound (I-j')

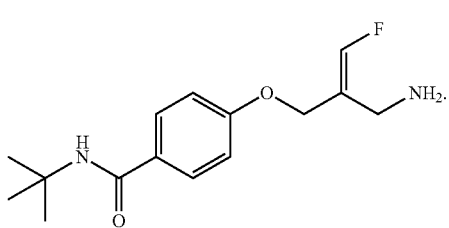

According to another embodiment,
step (S1) comprises the conversion of compound (I-j')

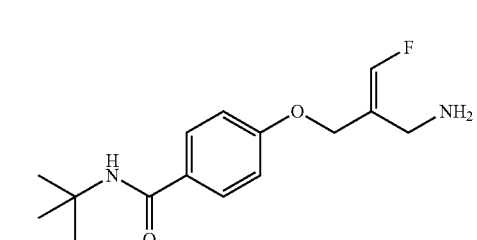

to compound (I-k)

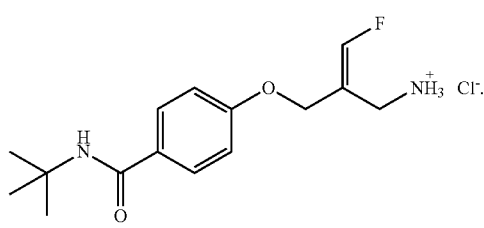

According to another embodiment,
compound (I-k) is obtained as Form I.

Preferred substituents of the compound of formula (IV)

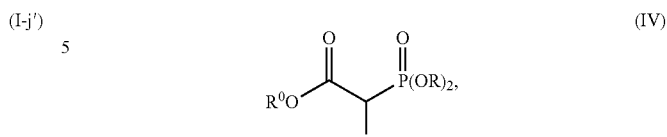

wherein Hal is defined as hereinbefore or hereinafter,
in step (S2) are as follows:
According to one embodiment,
R is selected from the group R-G1 consisting of
H, methyl, ethyl, n-propyl, iso-propyl, n-butyl, sec-butyl, iso-butyl, tert-butyl and phenyl,
wherein said methyl, ethyl, n-propyl, iso-propyl, n-butyl, sec-butyl, iso-butyl, tert-butyl and phenyl may be partially or fully halogenated, preferably fluorinated.
According to another embodiment,
R is selected from the group R-G2 consisting of
H and ethyl.
According to one embodiment,
$R^0$ is selected from the group $R^0$-G1 consisting of H and $C_{1-6}$-alkyl.
According to another embodiment,
$R^0$ is selected from the group $R^0$-G2 consisting of methyl, ethyl, n-propyl, iso-propyl, n-butyl, sec-butyl, iso-butyl and tert-butyl.
According to another embodiment,
$R^0$ is selected from the group $R^0$-G3 consisting of ethyl.
According to another embodiment,
in step (S2), the compound of formula (IV) is compound (IV-a)

According to one embodiment,
in step (S2), the compound of formula (III) is compound (III-g)

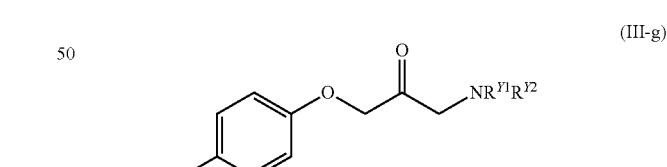

wherein $R^{ar}$ as well as $R^{Y1}$ and $R^{Y2}$ are defined as hereinbefore or hereinafter,
preferably $R^{ar}$ is selected from the group $R^{ar}$-G1 as defined hereinbefore, more preferably from the group $R^{ar}$-G2 as defined hereinbefore, wherein
$R^{N1}$ and $R^{N2}$ are preferably independently selected from the group $R^N$-G2 as defined hereinbefore, more preferably from the group $R^N$-G3 as defined hereinbefore, and
preferably $R^{Y1}$ and $R^{Y2}$ are independently selected from the group $R^Y$-G4a as defined hereinbefore or are selected from the group $R^Y$-G4b as defined hereinbefore, more preferably independently selected from the group $R^Y$-G5a as defined hereinbefore or are selected from the group $R^Y$-G5b as defined hereinbefore
and the compound of formula (II) is compound (II-g)

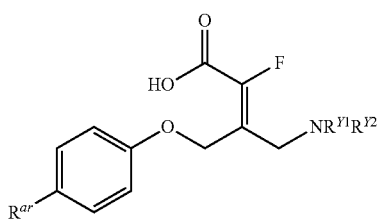
(II-g)

wherein $R^{ar}$ as well as $R^{Y1}$ and $R^{Y2}$ are defined as hereinbefore.

According to another embodiment,
in step (S2), the compound of formula (III) is compound (III-h)

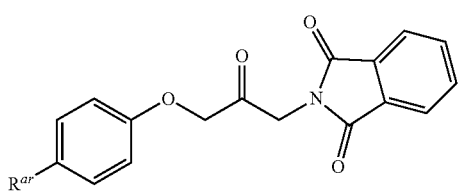
(III-h)

wherein $R^{ar}$ is selected from the group $R^{ar}$-G2 as defined hereinbefore in connection with $R^N$-G2 as defined hereinbefore,
and the compound of formula (II) is compound (II-h)

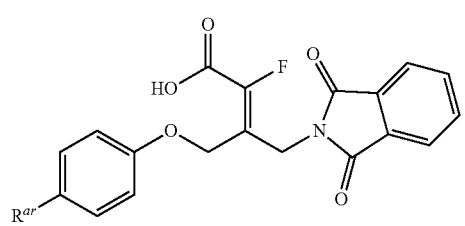
(II-h)

wherein $R^{ar}$ is defined as hereinbefore.

According to another embodiment,
in step (S2), the compound of formula (III) is compound

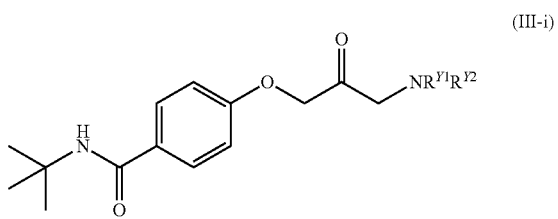
(III-i)

wherein $R^{Y1}$ and $R^{Y2}$ are independently selected from the group $R^Y$-G4a as defined hereinbefore or are selected from the group $R^Y$-G4b as defined hereinbefore, and the compound of formula (II) is compound (II-i)

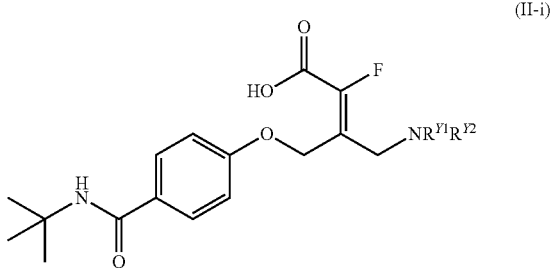
(II-i)

wherein $R^{Y1}$ and $R^{Y2}$ are defined as hereinbefore.

According to another embodiment,
in step (S2), the compound of formula (III) is compound (III-j)

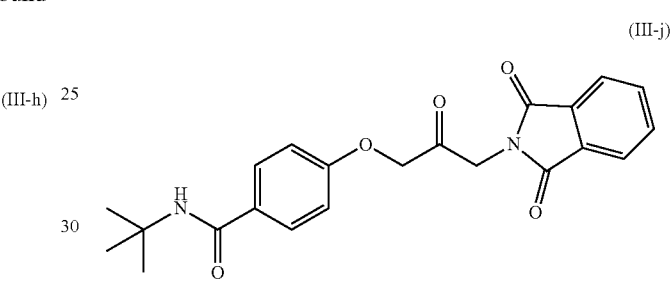
(III-j)

and the compound of formula (II) is compound (II-j)

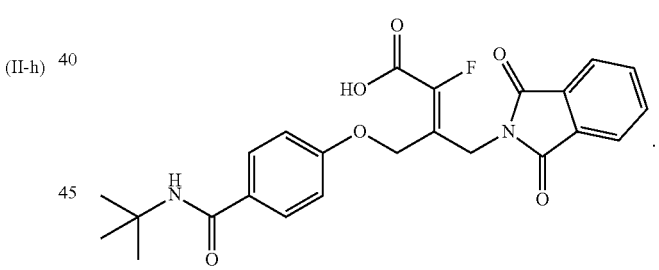
(II-j)

According to one embodiment,
step (S2) comprises the saponification of compound (II'-g)

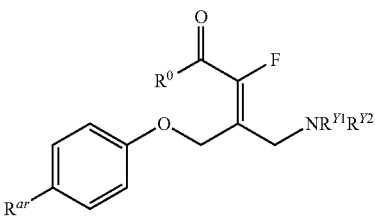
(II'-g)

wherein $R^0$, $R^{ar}$ as well as $R^{Y1}$ and $R^{Y2}$ are defined as hereinbefore or hereinafter, preferably R⁰ is selected from the group R⁰-G2 as defined hereinbefore, more preferably from the group R⁰-G3 as defined hereinbefore, and preferably $R^{ar}$ is selected from the group $R^{ar}$-G1 as defined hereinbefore, more preferably from the group $R^{ar}$-G2 as defined hereinbefore, wherein $R^{N1}$ and $R^{N2}$ are preferably independently selected from the group $R^N$-G2 as defined hereinbefore, more preferably from the group $R^N$-G3 as defined hereinbefore, and preferably $R^{Y1}$ and $R^{Y2}$ are independently selected from the group $R^Y$-G4a as defined hereinbefore or are selected from the group $R^Y$-G4b as defined hereinbefore, more preferably independently selected from the group $R^Y$-G5a as defined hereinbefore or are selected from the group $R^Y$-G5b as defined hereinbefore to compound (II-g)

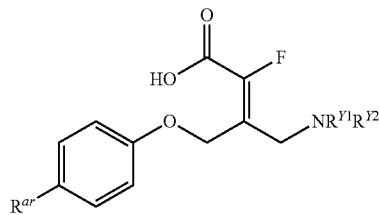

(II-g)

wherein $R^{ar}$ as well as $R^{Y1}$ and $R^{Y2}$ are defined as hereinbefore.

According to another embodiment, step (S2) comprises the saponification of compound (II'-h)

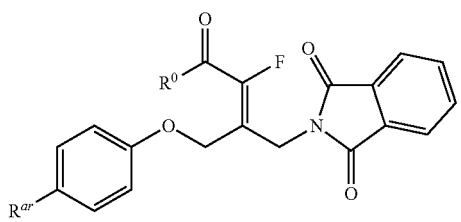

(II'-h)

wherein R⁰ is selected from the group R⁰-G2 as defined hereinbefore, and $R^{ar}$ is selected from the group $R^{ar}$-G2 as defined hereinbefore in connection with $R^N$-G2 as defined hereinbefore, to compound (II-h)

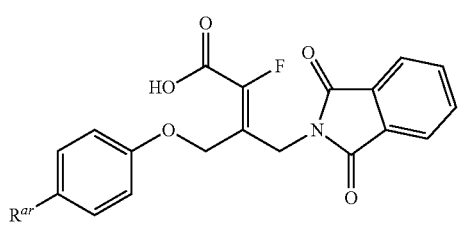

(II-h)

wherein $R^{ar}$ is defined as hereinbefore.

According to another embodiment, step (S2) comprises the saponification of compound (II'-i)

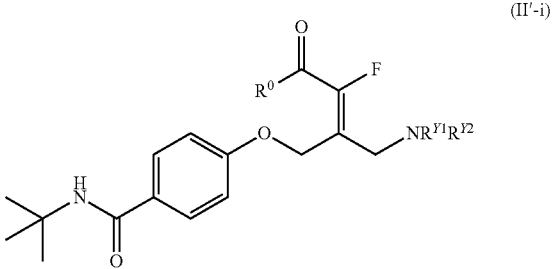

(II'-i)

wherein R⁰ is selected from the group R⁰-G2 as defined hereinbefore, and $R^{Y1}$ and $R^{Y2}$ are independently selected from the group $R^Y$-G4a as defined hereinbefore or are selected from the group $R^Y$-G4b as defined hereinbefore, to compound (II-i)

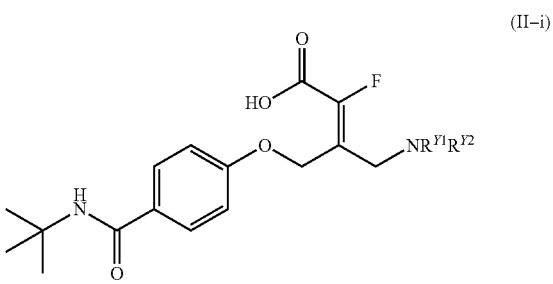

(II-i)

wherein $R^{Y1}$ and $R^{Y2}$ are defined as hereinbefore.

According to another embodiment, step (S2) comprises the saponification of compound (II'-j)

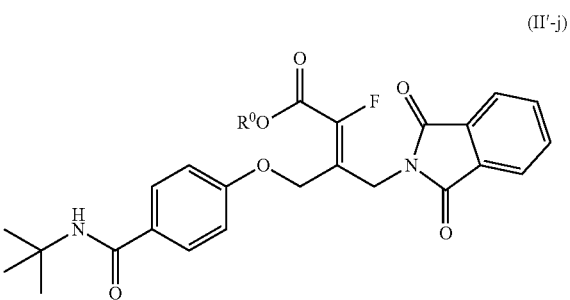

(II'-j)

wherein R⁰ is selected from the group R⁰-G2 as defined hereinbefore, to compound (II-j)

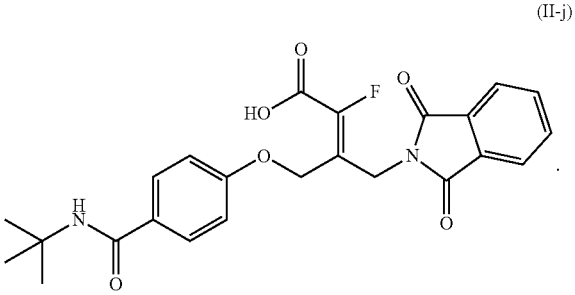 [SMILES: CC(C)(C)NC(=O)c1ccc(OC/C(CN2C(=O)c3ccccc3C2=O)=C(/F)C(=O)O)cc1]

(II-j)

According to another embodiment, in step (S2), the compound of formula (III) is compound (III-j)

(III-j)

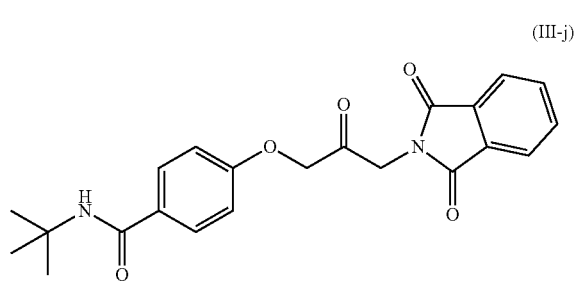 [SMILES: CC(C)(C)NC(=O)c1ccc(OCC(=O)CN2C(=O)c3ccccc3C2=O)cc1]

and the compound of formula (II') is compound (II'-k)

(II'-k)

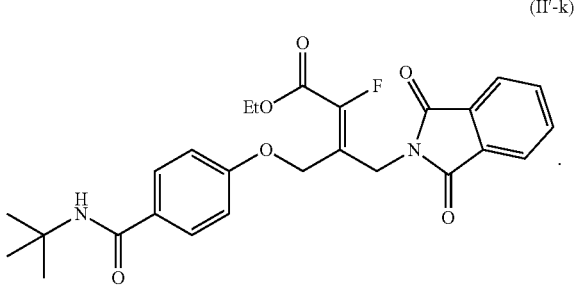 [SMILES: CCOC(=O)/C(F)=C(\COc1ccc(C(=O)NC(C)(C)C)cc1)CN1C(=O)c2ccccc2C1=O]

According to another embodiment,
step (S2) comprises the saponification of compound (II'-k)

(II'-k)

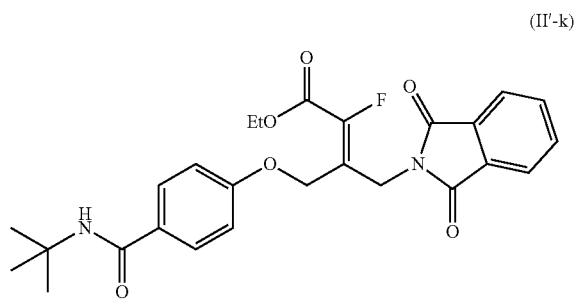

to compound (II-k)

(II-k)

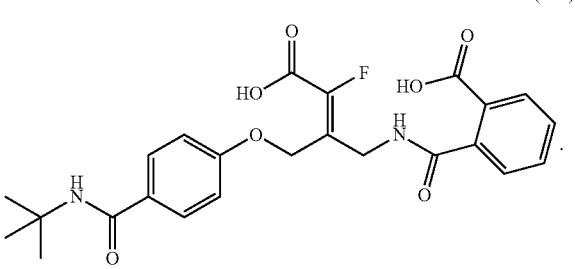

According to another embodiment,
step (S2) comprises the crystallization of compound (II-k)

(II-k)

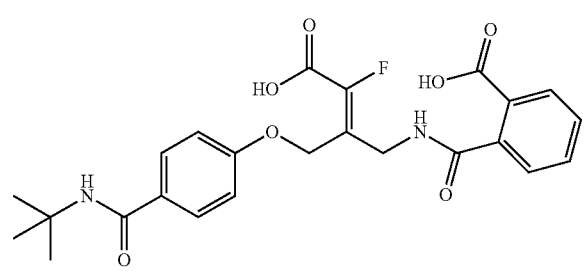

to improve the E/Z selectivity.

According to another embodiment,
step (S2) comprises the conversion of compound (II-k)

(II-k)

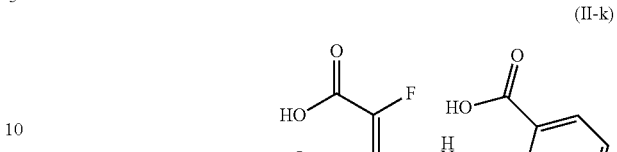

to compound (II-j)

(II-j)

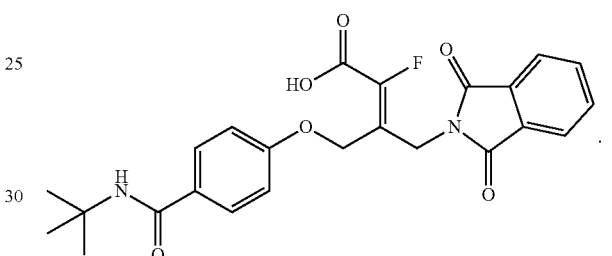

According to another embodiment,
in step (S1), the compound of formula (II) is compound (II-j)

(II-j)

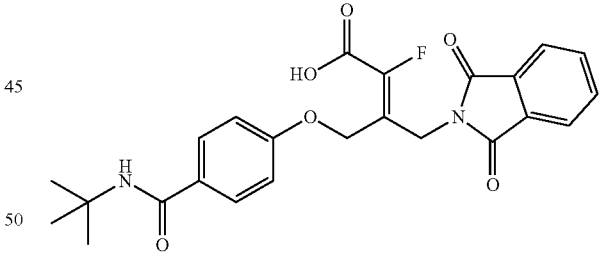

and the compound of formula (I) is compound (I-j)

(I-j)

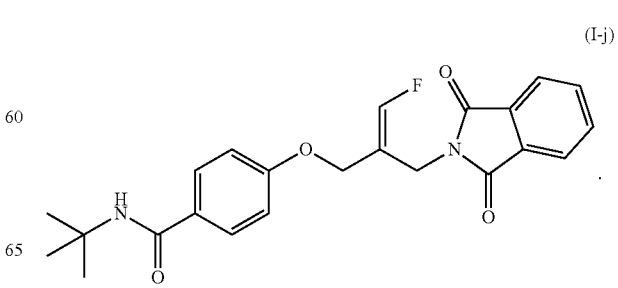

According to another embodiment,
step (S1) comprises the deprotection of compound (I-j)

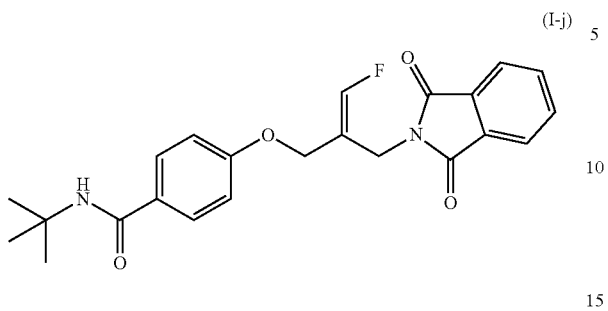

to compound (I-j')

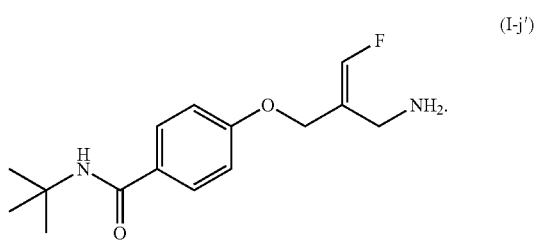 [SMILES: CC(C)(C)NC(=O)c1ccc(OC/C(=C/F)CN)cc1]

According to another embodiment,
step (S1) comprises the conversion of compound (I-j')

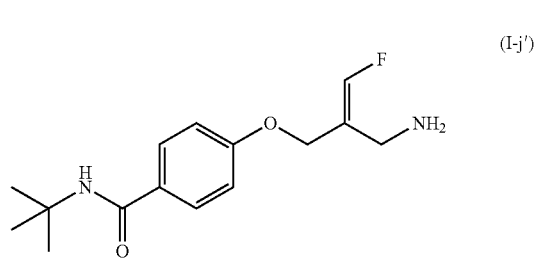 [SMILES: CC(C)(C)NC(=O)c1ccc(OC/C(=C/F)CN)cc1]

to compound (I-k)

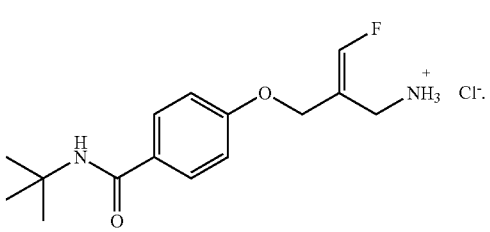

In a second aspect, the present invention relates to the intermediates that are comprised in the method according to the first aspect of the invention.

Thus, the invention relates to intermediates of formulas (III), (II'), (II), and (I)

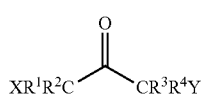

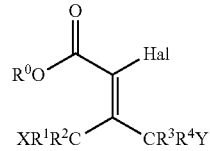

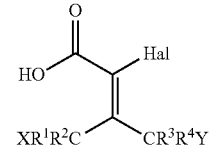

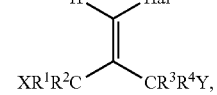

in particular to intermediates of formulas (II') and (II),
wherein Hal, R, $R^0$, $R^1$, $R^2$, $R^3$, $R^4$, X and Y are defined as for the first aspect of the present invention.

Particularly, the invention relates to those intermediates of formulas (III), (II'), (II), and (I) that are described above in the embodiments of the first aspect of the invention.

According to one embodiment,
the intermediate of formula (III) is compound (III-j)

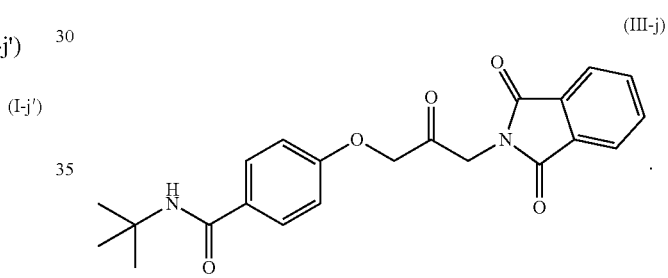

According to one embodiment,
the intermediate of formula (II') is compound (II'-g) as defined hereinbefore.
According to another embodiment,
the intermediate of formula (II') is compound (II'-h) as defined hereinbefore.
According to another embodiment,
the intermediate of formula (II') is compound (II'-i) as defined hereinbefore.
According to another embodiment,
the intermediate of formula (II') is compound (II'-j) as defined hereinbefore.
According to another embodiment,
the intermediate of formula (II') is compound (II'-k)

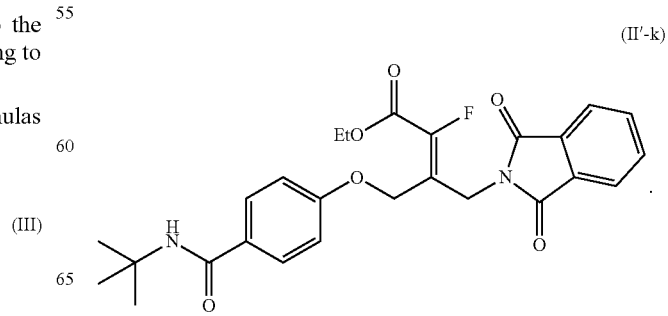

According to one embodiment, the intermediate of formula (II) is compound (II-g) as defined hereinbefore.

According to another embodiment, the intermediate of formula (II) is compound (II-h) as defined hereinbefore.

According to another embodiment, the intermediate of formula (II) is compound (II-i) as defined hereinbefore.

According to another embodiment, the intermediate of formula (II) is compound (II-j)

(II-j)

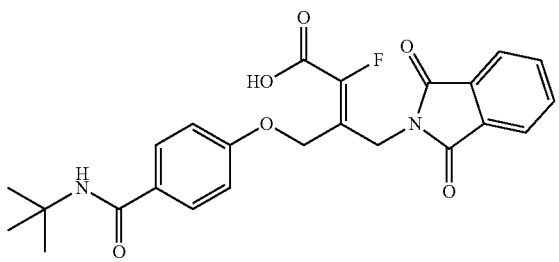

According to another embodiment, the intermediate of formula (II) is compound (II-k)

(II-k)

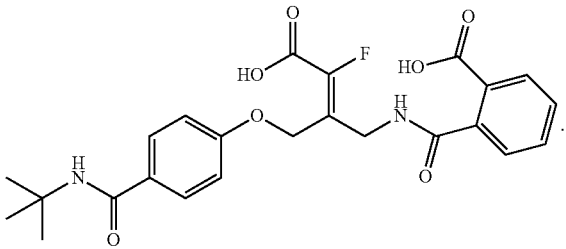

According to one embodiment, the intermediate of formula (I) is compound (I-g) as defined hereinbefore.

According to another embodiment, the intermediate of formula (I) is compound (I-g') as defined hereinbefore.

According to another embodiment, the intermediate of formula (II) is compound (I-h) as defined hereinbefore.

According to another embodiment, the intermediate of formula (II) is compound (I-h') as defined hereinbefore.

According to another embodiment, the intermediate of formula (II) is compound (I-i) as defined hereinbefore.

According to one embodiment, the intermediate of formula (I) is compound (I-j)

(I-j)

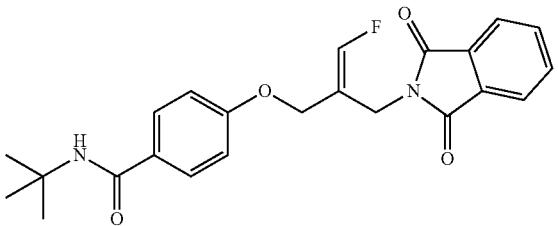

According to another embodiment, the intermediate of formula (I) is compound (I-j')

(I-j')

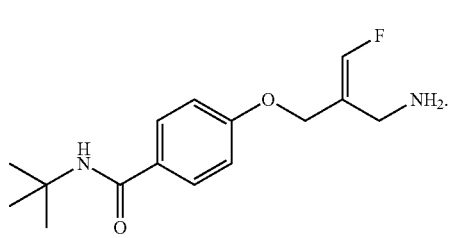

EXAMPLES AND EXPERIMENTAL DATA

The following abbreviations are used hereinbefore and hereinafter:
Ac acetyl
Boc tert-butyloxycarbonyl
Bu butyl
equiv. molar equivalents
Et ethyl
DBU 1,8-diazabicyclo(5.4.0)undec-7-ene
DMAC N,N-dimethylacetamide
DME dimethyl ether
DMF N,N-dimethylformamide
DMSO dimethyl sulfoxide
DSC differential scanning calorimetry
EtOAc ethyl acetate
h hour
HMDS hexamethyldisilazide (bis(trimethylsilyl)amide)
HPLC high-performance liquid chromatography
HWE reaction Horner-Wadsworth-Emmons reaction
IPC in-process control
i-Pr iso-propyl
MCH methyl cyclohexane
Me methyl
2-MeTHF 2-methyl-tetrahydrofuran
MTBE methyl tert-butyl ether
n-Bu n-butyl
NMP N-methylpyrrolidinone
Ph phenyl
ssNMR solid-state nuclear magnetic resonance
t-Bu tert-butyl
Tc thiophene-2-carboxylate
Tf triflyl (trifluoromethanesulfonyl)
THF tetrahydrofuran
XRPD X-ray powder diffraction (1) Procedure for the Formation of (III-j)
a) Preparation of (VII-j) (Route A)

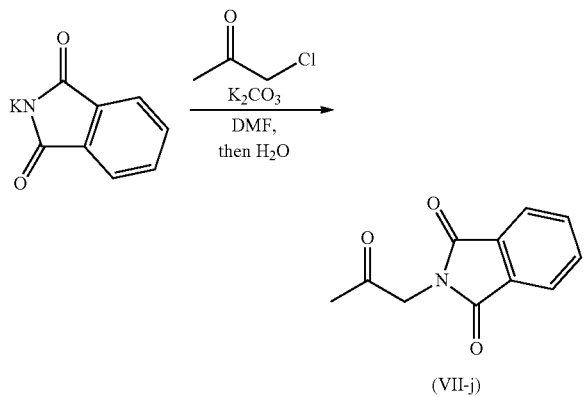

(VII-j)

A mixture of potassium phthalimide (100.0 g, 539.9 mmol, 1.0 equiv.), potassium carbonate (11.2 g, 81.0 mmol, 0.15 equiv.) and N,N-dimethylformamide (DMF) (200 mL) is treated with chloroacetone (47.3 mL, 54.9 g, 593.9 mmol, 1.1 equiv.) at a rate to control the internal temperature at not more than 40° C. After the addition is complete, the reaction mixture is stirred for about 12 hours at about 20-25° C. Water (333 mL) is charged to the reaction mixture at a rate to control the internal temperature at not more than 30° C. The mixture is stirred at about 20-25° C. for about 1 hour, and then the mixture is filtered. The filter cake is washed with water (200 mL), and the product is dried at about 70-80° C. under vacuum with a nitrogen flow for about 12 hours. The product phthalimidoacetone (VII-j) is obtained as a white solid (90.2 g, 97.3 wt. % purity, 80% yield).

b) Preparation of (VII-j) (Route B)

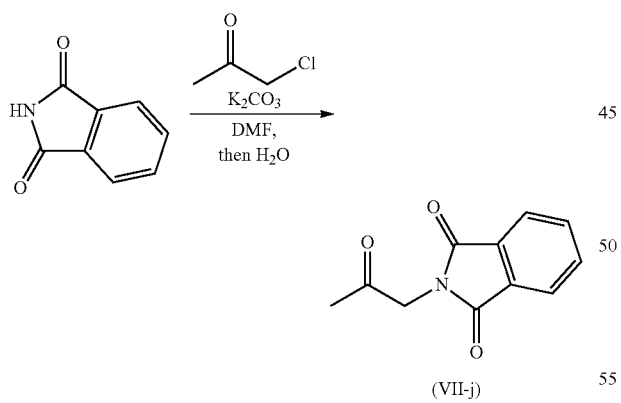

(VII-j)

A mixture of phthalimide (110.4 kg, 750.5 mol, 1.0 equiv.), potassium carbonate (59.2 kg, 428.4 mol, 0.57 equiv.) and DMF (195 kg) is heated to 60-70° C. and stirred at this temperature for at least 10 minutes. The solution is cooled to 50-60° C. and chloroacetone (80.0 kg, 864.9 mol, 1.15 equiv.) is added over a period of 1 hour at a temperature of 50-70° C. The reaction mixture is heated to 80-86° C. and stirred at this temperature for at least 90 minutes. An in-process control (IPC) sample is taken at 80-86° C. to measure the conversion (criterion ≤3.0 area % of phthalimide, result 0.0 area % after 3 hours). The reaction mixture is transferred to a second reactor and the first reactor is rinsed into the latter with DMF (60 kg). The reaction mixture is then heated to 30-70° C. and water (576 L) is added to keep the inner temperature at about 50° C. The suspension is cooled to 0-10° C. and stirred at this temperature of at least 1 h, and then filtered. The filter cake is washed with water (4×50 L) and the product is dried at about 70-80° C. under vacuum for about 12 hours. The product phthalimidoacetone (VII-j) is obtained as a white crystalline solid (147.0 kg, organic purity HPLC: 99.8 area %, yield: 96.5%).

c) Preparation of (VI-j) (Route A)

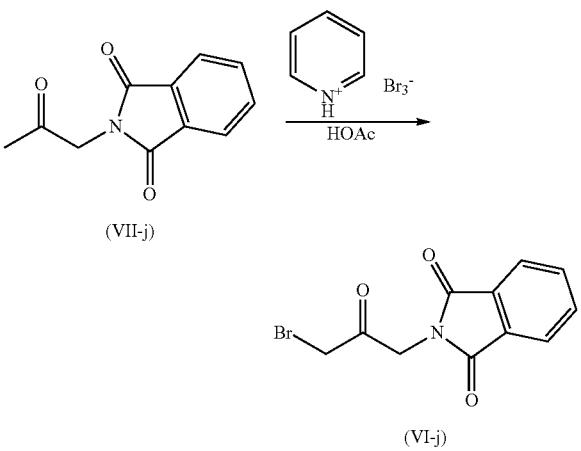

(VI-j)

A mixture of phthalimidoacetone (100.0 g, 492.2 mmol, 1.0 equiv.), pyridinium hydrobromide perbromide (192.4 g, 90 wt. % purity, 541.4 mmol, 1.1 equiv.) and acetic acid (400 mL) is stirred for about 12 hours at about 20-25° C. Water (400 mL) is charged to the reaction mixture at a rate to control the internal temperature at not more than 30° C. The mixture is stirred at about 20-25° C. for about 2 hours, and then the mixture is filtered. The filter cake is washed with water (400 mL), and the product is dried at about 50-60° C. under vacuum with a nitrogen flow for about 12 hours. The crude product is then recrystallized in toluene (400 mL) by heating to about 90° C. for about 30 minutes, cooling back to 20-25° C. and holding at this temperature for about 2 hours, and then filtering the solid, washing the solid with toluene/heptane 1:2 v/v (100 mL) and heptane (100 mL), and finally drying at 20-30° C. under vacuum to provide the purified product (VI-j) as a white solid (94.0 g, 96.0 wt. % purity, 65% yield).

d) Preparation of (VI-j) (Route B)

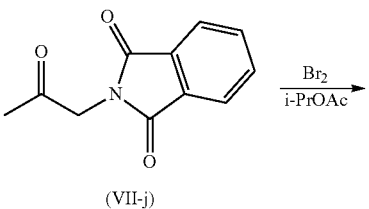

(VII-j)

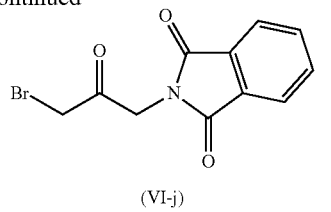

(VI-j)

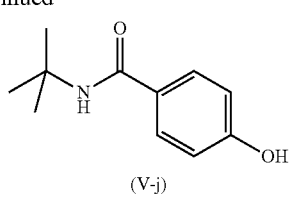

(V-j)

A mixture of phthalimidoacetone (140.0 kg, 689.0 mol, 1.0 equiv.) and i-PrOAc (957 kg) is heated to 30-50° C. Bromine (110.1 kg, 689.0 mol, 1.0 equi.) is added to keep the inner temperature at 30-50° C. The reaction mixture is stirred for 6-14 h at 30-50° C. The reaction mixture is cooled to 15-25° C. and stirred at this temperature for 12-18 h. The reaction mixture is transferred to a second reaction vessel and rinsed with i-PrOAc (261 kg). The reaction mixture is heated to 60-70° C. and pre heated (50-70° C.) water (420 kg) is added to the reaction mixture to keep its inner temperature of 50-70° C. The reaction mixture is heated to 65-71° C. and stirred for 10 min at this temperature. The aqueous phase is separated from the organic phase at 65-71° C. Pre-heated (50-70° C.) water (420 kg) is added to the organic phase at 50-70° C. The biphasic mixture is heated to 65-71° C. and stirred for 10 min at this temperature. The aqueous phase is separated from the organic phase at 65-71° C. The organic phase is heated to 70-80° C. and solvent (980 L) is distilled off under vacuum at 70-85° C. The residual product solution is heated to 67-73° C. and seed crystals (200 g) are added. The thin product suspension is stirred at 67-73° C. for 30-120 min before it is cooled to −15 to −5° C. within 120 min and stirred at this temperature for 60-180 min and then filtered. The filter cake is washed with methyl cyclohexane (MCH) (354 kg) and the product is dried at about 60° C. under vacuum for about 2-3 h. The product 2-(4-bromo-3-oxobutyl)-1H-isoindole-1,3(2H)-dione (VI-j) is obtained as a white crystalline solid (153.7 kg, organic purity HPLC: 94.5 area %, yield: 75.3%).

Optional recrystallization procedure for 2-(4-bromo-3-oxobutyl)-1H-isoindole-1,3(2H)-dione:

A mixture of 2-(4-bromo-3-oxobutyl)-1H-isoindole-1,3(2H)-dione (20.0 g, 71.7 mmol, 1.0 equiv.) and toluene (80 mL) is heated to 105° C. and stirred for 10-20 min at this temperature. The temperature of the formed solution is decreased to 90° C. and seed crystals are added. The formed suspension is stirred for 25-35 min at 90° C. The suspension is cooled to 15-25° C. over a period of 90 min and stirred at 15-25° C. for another 90 min and then filtered. The filter cake is washed with a mixture of toluene/MCH (29.6 mL/32 mL) and then MCH (32 mL) and the product is dried at about 60° C. under vacuum for about 5 h. The product is obtained as a white crystalline solid (18.2 g, organic purity HPLC: 98.0 area %, yield: 91%).

e) Preparation of (V-j)

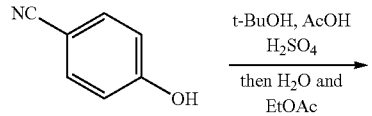

A mixture of 4-hydroxybenzonitrile (200.0 g, 1.68 mol, 1.0 equiv.) and glacial acidic acid (420.4 g, 7.00 mol, 4.2 equiv.) is stirred at room temperature for 5 min tert-butanol (236.5 g, 3.19 mol, 1.9 equiv.) is added (slightly endothermic) and the mixture is stirred at 15-25° C. for 30 min.

Concentrated sulfuric acid (247.0 g, 2.52 mol, 1.5 equiv.) is added over a period of about 130 min at an inner temperature of 18-30° C. The reaction mixture is heated to 40° C. in about 30 min and stirred at this temperature for 60 min. An IPC sample is taken at 40° C. to measure the conversion (criterion ≤1.0 area % of 4-hydroxybenzonitrile, result 0.61 area % after 1 hours). To the reaction mixture ethyl acetate (300 mL) is added at 40° C. followed by water (440 mL) over 20 min and stirred at this temperature for 10 min. Seed crystals are added. The formed suspension is stirred for 10 min at 40° C. The resulting suspension is cooled to 20° C. in 90 min. To the suspension water (360 mL) is added at this temperature over 15 min. The suspension is cooled to −5 to 5° C. and stirred for 120 min at this temperature and then filtered. The filter cake is washed with water (3×400 mL) and the product is dried at about 70° C. under vacuum for about 26 h. The product (V-j) is obtained as a white crystalline solid (278.5 g, organic purity HPLC: 99.9 area %, yield: 85.8%).

Optional recrystallization procedure for (V-j):

A mixture of (V-j) (20.0 g, 0.10 mol, 1.0 equiv.) and acetonitrile (110 mL) is heated to 80° C. and stirred for 15 min at this temperature. The temperature of the formed solution is decreased to 70° C. and seed crystals are added. The formed suspension is stirred for 30 min at 70° C. The suspension is cooled to 20° C. over a period of 120 min. The suspension is cooled to 5° C. over a period of 30 min and stirred for another 60 min and then filtered. The filter cake is washed with cold acetonitrile (3×30 mL) and the product is dried at about 60° C. under vacuum for about 12 h. The product (V-j) is obtained as a white crystalline solid (18.0 g, organic purity HPLC: 99.97 area %, yield: 90.1%).

f) Preparation of (III-j) (Route A)

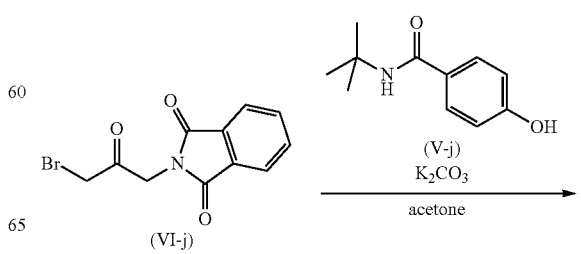

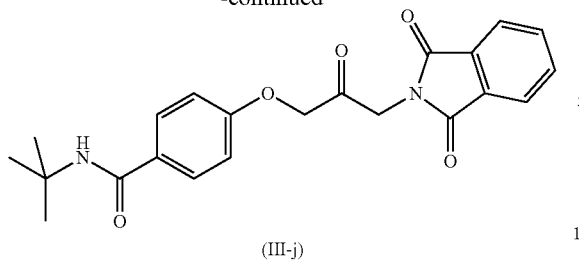

(III-j)

A mixture of (VI-j) (100.0 g, 354.5 mmol, 1.0 equiv.), (V-j) (75.4 g, 389.9 mmol, 1.1 equiv.), potassium carbonate (53.9 g, 389.9 mmol, 1.1 equiv., 325 mesh) and acetone (600 mL) is stirred for about 12 hours at about 20-25° C. Water (600 mL) is charged to the reaction mixture at a rate to control the internal temperature at not more than 30° C. The mixture is stirred at about 20-25° C. for about 1 hour, and then the mixture is filtered. The filter cake is washed with water (200 mL) followed by heptane (200 mL) and the product is dried at about 80-90° C. under vacuum with a nitrogen flow for about 12 hours. The product (III-j) is obtained as a tan solid (109.5 g, 95.8 wt. % purity, 75% yield).

g) Preparation of (III-j) (Route B)

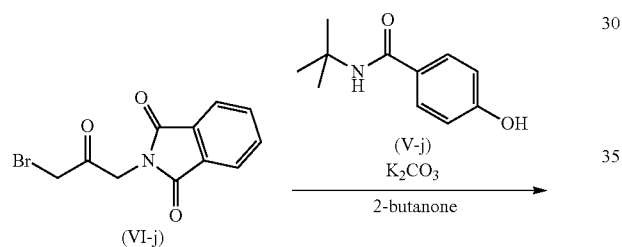

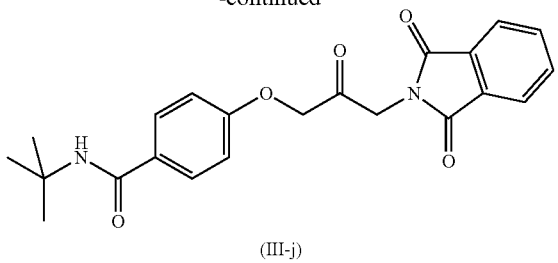

(III-j)

A mixture of compound (V-j) (107.9 g, 558.0 mmol, 1.05 equiv.), compound (VI-j) (150.0 g, 532.0 mmol, 1.0 equiv.) and potassium carbonate (77.5 g, 561.0 mmol, 1.05 equiv.) in 2-butanone (1200 mL) is stirred for 10 min at room temperature before it is heated to 70° C. over a period of 180 min. After the 70° C. is reached, an IPC sample is taken to measure the conversion (criterion ≤2.5 area % of (VI-j), result 0.9 area %). After cooling to 30-45° C. water (620 mL) is added to the suspension and stirred for about 5 min. The aqueous phase is separated from the organic phase. From the organic phase solvent (520 mL) is distilled off. Methanol (MeOH) (1000 mL) is added and solvent (885 mL) is distilled off under vacuum again. MeOH (800 mL) is added a second time and solvent (780 mL) is distilled off under vacuum. At a temperature of not less than 50° C., methyl tert-butyl ether (MTBE) (615 mL) is added and the mixture is cooled to −5° C. and stirred for 90 min at this temperature. The suspension is then filtered. The filter cake is washed with MeOH (65 mL) and then MTBE (2×130 mL) and the product is dried at about 65° C. under vacuum for about 12 h. The product (III-j) is obtained as a white crystalline solid (168.3 g, organic purity HPLC: 99.3 area %, yield: 80.2%).

(2) Procedure for the Formation of (II j) (Horner-Wadsworth-Emmons (HWE) Reaction)

a) Preparation of (II-k) (Route A)

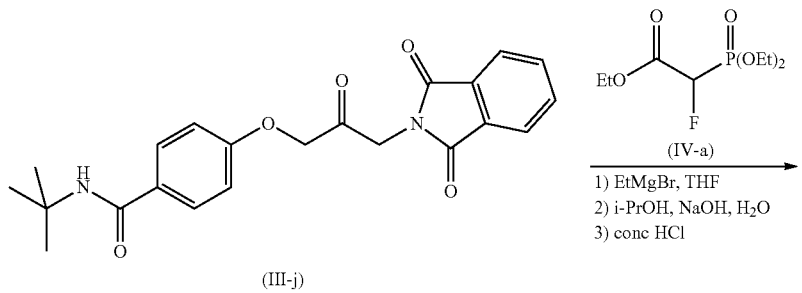

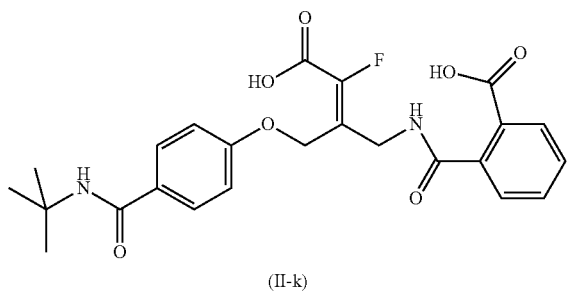

(II-k)

A solution of (IV-a) (104.4 g, 431.0 mmol, 1.7 equiv.) and THF is cooled to about −10° C. and treated with EtMgBr solution (431.0 mL, 431.0 mmol, 1.7 equiv., 1.0 M solution in THF) at a rate to maintain the temperature below 10° C. In a separate reactor, (III-j) (100.0 g, 253.5 mmol, 1.0 equiv.) and THF (1000 mL) are charged, and the resultant slurry is heated to about 40° C. The solution of the anion of (IV-a) in THF is added to the warm slurry of (III-j) in THF at a rate to maintain the temperature of the batch between 40-55° C. After the addition is complete, the batch is maintained for about 1 hour at about 40° C. About 1200 mL of THF is then distilled out, and isopropanol (800 mL) is added. The distillation is continued to remove about 600 mL of solvent. Isopropanol (400 mL) is added, followed by a solution of sodium hydroxide (60.85 g, 1521.2 mmol, 6 equiv.) in water (450 mL). The reaction mixture is stirred at about 25° C. for about 1 hour. Concentrated hydrochloric acid (147.8 mL, 1799.9 mmol, 7.1 equiv.) is added at a rate to control the temperature below 35° C. The resultant slurry is stirred at about 20-25° C. for about 12 hours, and then the mixture is filtered. The filter cake is washed with a mixture of isopropanol and water, 2:1 by volume (300 mL) and the product is dried at about 50-65° C. under vacuum with a nitrogen flow for about 12 hours. The product (II-k) is obtained as a white solid (82.8 g, 94.0 wt. % purity, 65% yield, E/Z ratio=97:3).

b) Preparation of (II-k) (Route B)

temperature below 10° C. The mixture is heated to about 20° C. and stirred at this temperature for not less than 30 min. In a second reactor (III-j), 2-Methyl-THF (40 mL) and THF (10 mL) are added and the suspension is heated to about 35° C. At this temperature the content of the first reactor (deprotonated (IV-a)) is added at 35±5° C. (below 40° C./preferred 35° C.) and the first reactor is rinsed with 2-Methyl-THF (10 mL) into the second reactor.

The solution is stirred for not less than 30 min at about 35° C. An IPC sample is taken to measure the conversion (criterion ≤1.0 area % of (III-b), result 0.42 area %). Citric acid (10% aqueous solution, 60 mL) is added at about 35° C. After 15 min of stirring at about 35° C., the aqueous phase is separated from the organic phase. A second portion of citric acid (10% aqueous solution, 60 mL) is added at about 35° C. and after 15 min of stirring the aqueous phase is separated from the organic phase again. Solvent (75 mL) is distilled off under vacuum from the organic phase. Isopropanol (80 mL) is added and solvent (75 mL) is distilled off under vacuum again. Isopropanol (80 mL), Water (40 mL) is added at about 35° C. followed by sodium hydroxide added at 40±5° C. (below 45° C./preferred 40° C.) (45% aqueous solution, 18.0 g, 203 mmol, 4.0 equiv.).

Water (10 mL) is added at about 45° C. An IPC sample is taken to measure the conversion (criterion ≤1.0 area % of the ethyl ester of (II-k), result <0.1 area %). The reaction mixture is cooled to about 20° C. and hydrochloric acid (36%, 15.4 g, 152.1 mmol, 3.0 equiv.) is added. Seed crystals are added at 20° C. and the resulting suspension is stirred for 60 min at this temperature.

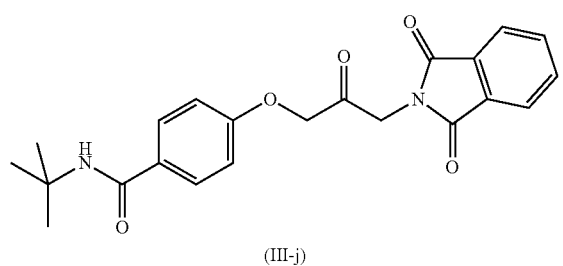

(III-j)

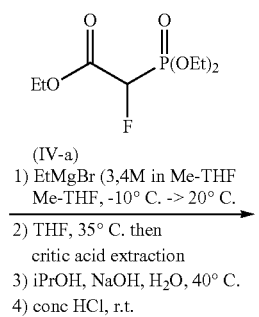

(IV-a)

1) EtMgBr (3,4M in Me-THF Me-THF, -10° C. -> 20° C.
2) THF, 35° C. then critic acid extraction
3) iPrOH, NaOH, H₂O, 40° C.
4) conc HCl, r.t.

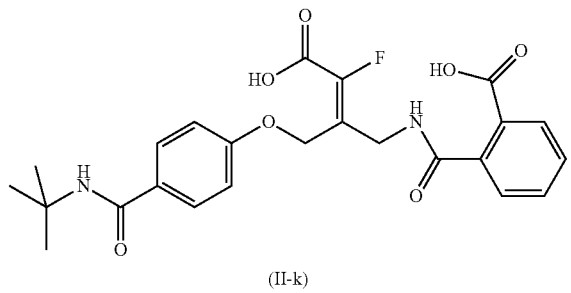

(II-k)

2-Methyl-THF (40 mL) is cooled to −10° C. under nitrogen and EtMgBr (40% in 2-Methyl-THF, 25.3 g, 76.1 mmol, 1.5 equiv.) is added to keep the inner temperature below 10° C. The reaction mixture is cooled to −10° C. and (IV-a) is added to keep the inner Hydrochloric acid (36%, 7.7 g, 76.1 mmol, 1.5 equiv.) and water (16 mL) are added and stirred for another 60 min at 20° C. before the suspension is filtered. The filter cake is washed with water (40 mL) and two times with isopropanol (40 mL each wash) and the product is dried at about 60° C. under vacuum for about 12 h. The product is obtained as an off-white crystalline solid (16.2 g, organic purity: 96.1 area %, E/Z ratio: 96.4/3.6 area %, yield: 67.7%).

c) Preparation of (II-j) (Route A)

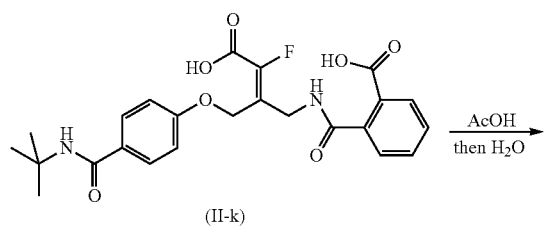
(II-k)

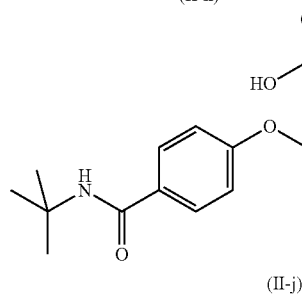
(II-j)

A mixture of (II-k) (100.0 g, 211.7 mmol, 1.0 equiv.) and acetic acid (400 mL) is heated at about 110° C. for about 7 hours. About 200 mL of acetic acid is then distilled out under slight vacuum, and the mixture is then cooled to about 25° C. Water (400 mL) is charged to the reaction mixture over about 1 hour at a rate to control the internal temperature at not more than 25° C. The mixture is stirred at about 20-25° C. for about 3 hours, and then the mixture is filtered. The filter cake is washed with water (400 mL) followed by heptane (200 mL) and the product is dried at about 50-60° C. under vacuum with a nitrogen flow for about 12 hours. The product (II-j) is obtained as a tan solid (89.3 g, 97.0 wt. % purity, 90% yield).

d) Preparation of (II-j) (Route B)

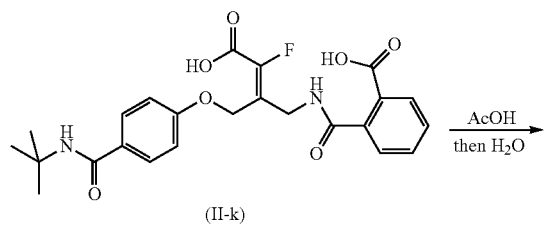
(II-k)

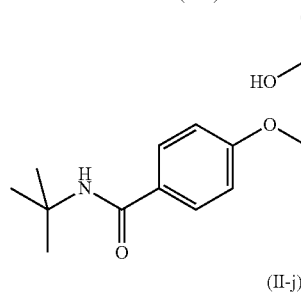
(II-j)

A mixture of (II-k) (80.0 g, 169.0 mmol, 1.0 equiv.) and acetic acid (320 mL) is heated rapidly to 115° C. and stirred at this temperature for at least 3.5 h. Water (320 mL) is added over a period of 30 min at a temperature of 90-115° C. The suspension is cooled to room temperature over a period of 120 min.

The product suspension is further stirred for 2 h at room temperature before it is filtered.

The filter cake is washed with water (160 mL) and MTBE (160 mL) and the product is dried at about 60° C. under vacuum for about 5 h. The product is obtained as an off-white crystalline solid (63.4 g, organic purity HPLC: 99.7 area %, yield: 82.4%).

(3) Procedure for the Formation of (I-j)

a) Preparation of (I-j) (Protodecarboxylation of (II-j)) (Route A)

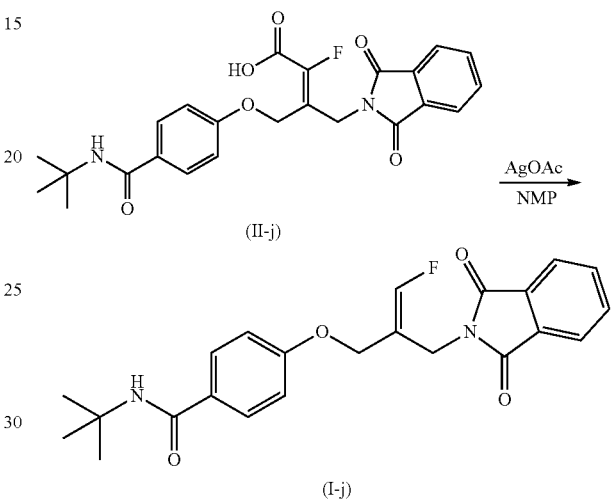

A mixture of (II-j) (100.0 g, 220.0 mmol, 1.0 equiv.) and NMP (185 mL) is heated to about 130° C. A slurry of silver(I) acetate (1.84 g, 11.0 mmol, 0.05 equiv.) in NMP (15 mL) is added, and the reaction mixture is aged at about 130° C. for about 3 hours. The mixture is then cooled to about 20-25° C. Ethyl acetate (250 mL) and diatomaceous earth (Celite®) (10.0 g) are added, and the mixture is stirred at 20-25° C. for about 1 hour. The mixture is then filtered through a pad of Celite, and the pad is rinsed with EtOAc (2×100 mL). The combined filtrates are distilled to remove EtOAc (about 450 mL) at about 40-45° C. under vacuum. The mixture is cooled to about 20-25° C. A solution of sodium thiosulfate pentahydrate (70.6 g) in water (380 mL) is added over 1 hour, and the mixture is stirred at 20-25° C. for about 12 hours, and then filtered. The filter cake is washed with water (3×300 mL) followed by heptane (300 mL) and the product is dried at about 50-60° C. under vacuum with a nitrogen flow for about 12 hours. The product (I-j) is obtained as a tan solid (89.3 g, 97.1 wt. % purity, 96% yield).

b) Preparation of (I-j) (Protodecarboxylation of (II-j)) (Route B)

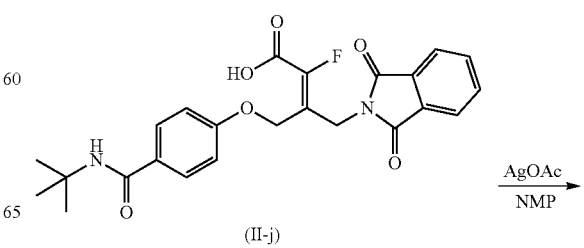
(II-j)

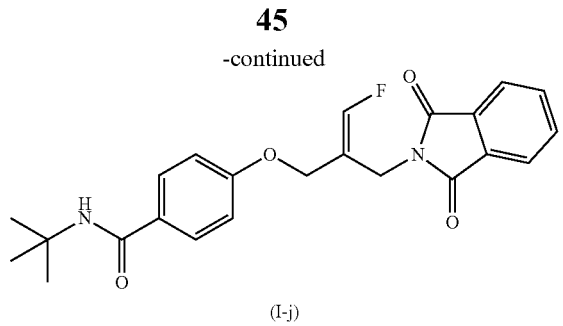

(I-j)

A mixture of (II-j) (35.0 g, 77.0 mmol, 1.0 equiv.) and silver(I) acetate (0.95 g, 6 mmol, 0.075 equiv.) is suspended in NMP (52.5 mL), then heated to about 130-140° C. The reaction mixture is aged at about 130-140° C. for about 3 hours. An IPC sample is taken to measure the conversion (criterion ≤1.0 area % of (II-j)).

The mixture is then cooled to about 20-25° C. Ethyl acetate (70 mL), diatomaceous earth (Celite®) (0.85 g) and activated carbon (0.85 g) are added, and the mixture is stirred at 20-25° C. for about 5-30 min. The mixture is then filtered through a depth filter sheet (KD 7), then the filter is rinsed with EtOAc (35 mL). The combined filtrates are distilled to remove EtOAc (about 105 mL) at about 80° C. under vacuum. The mixture is heated to about 60° C. then MeOH (52.5 mL) and water (52.5 mL) are added. The solution is cooled to 55-50° C., then seeded with (I-j) and cooled to 45-40° C. in about 45 min Water (52.5 mL) is added over a period of about 30 min and the suspension is cooled to 5-10° C. and stirred for about 30 min and then filtered. The filter cake is washed with a mixture of water (35 mL) and MeOH (35 ml) followed by water (35 mL) and the product is dried at about 75° C. under vacuum for about 12 h. The product (I-j) is obtained as a tan solid (30.4 g, organic purity HPLC: 99.9%, 96.0% yield).

(4) Screening of Conditions for the Protodecarboxylation

For the protodecarboxylation of (II-j), various copper and silver catalysts were tested in different solvents and at different temperatures.

A reaction vial was charged with compound (II-j) (70 mg, 0.15 mmol), a copper or silver species (50 mol %, unless stated otherwise), and reaction solvent (1 mL). The vial was inverted three times by evacuating and breaking the vacuum with argon. The reaction vial was then placed into an oil bath preheated to the reaction temperature. The reaction mixture was stirred for 1-22 h under positive argon pressure.

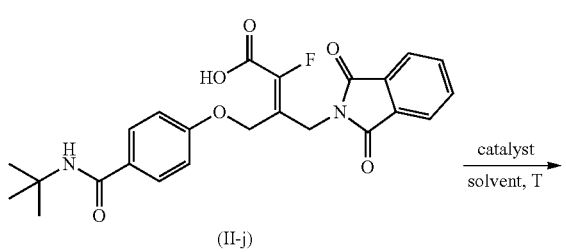

(II-j)

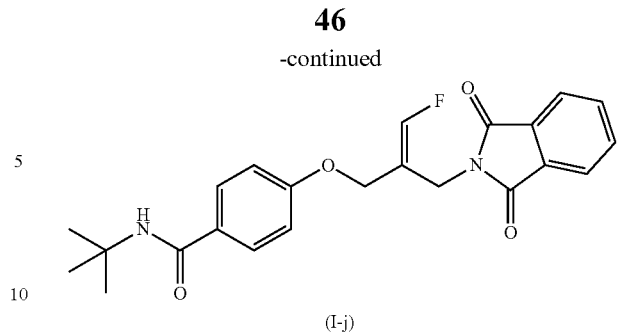

(I-j)

a) Catalyst and Solvent Screening

| Catalyst | Solvent | T [° C.]* | Conversion [%], (time) |
|---|---|---|---|
| Cu₂O | Pyridine | 120 | 100 (5 h) |
| Cu₂O | NMP | 120 | 96 (22 h) |
| CuOAc | Pyridine | 120 | 65 (22 h) |
| CuTc | Pyridine | 120 | 91 (5 h) |
| Ag₂CO₃ | Pyridine | 120 | 100 (18 h) |
| Ag₂CO₃ | NMP | 120 | 100 (1.5 h) |
| Ag₂CO₃ | DMAC | 120 | 100 (1.5 h) |
| Ag₂CO₃ | CH₃CN** | 90 | 97 (24 h) |

*oil bath temperature
**sealed vial b) Silver Catalyst Screening

| Catalyst | Solvent | T [° C.] | Conversion [%)] (time) |
|---|---|---|---|
| Ag₂O | NMP | 120 | 100 (1 h) |
| AgOAc | NMP | 120 | 100 (1 h) |
| AgNO₃ | NMP | 120 | 100 (2.5 h) | c) Screening of Catalyst Loading

| Catalyst | Loading [mol %] | Solvent | T [° C.] | Conversion [%], (time) |
|---|---|---|---|---|
| Ag₂CO₃ | 50 | NMP | 120 | 100 (1.5 h) |
| Ag₂CO₃ | 10 | NMP | 120 | 100 (3 h) |
| Ag₂CO₃ | 5 | NMP | 120 | 100 (4.0 h) |
| AgOAc | 50 | NMP | 120 | 100 (1 h) |
| AgOAc | 10 | NMP | 120 | 100 (2.5 h) |
| AgOAc | 5 | NMP | 120 | 53 (7 h) |
| AgOAc | 5 | NMP* | 130 | 100 (2.5 h) |
| AgOAc | 2.5 | NMP | 120 | 26 (7 h) |

*only two volume equivalents of NMP used (instead of 4 volume equivalents as for the other tests)

(5) Procedure for the Formation of (I-j')

a) Preparation of (I-j') (Deprotection of (I-j)) (Route A)

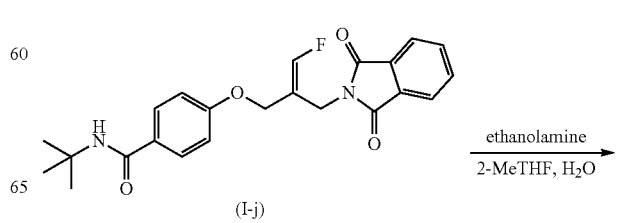

(I-j) →(ethanolamine / 2-MeTHF, H₂O)

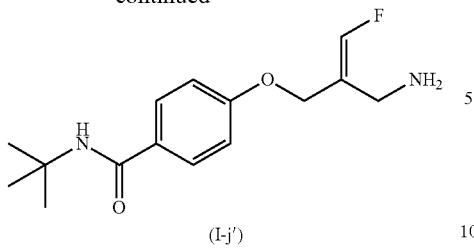

(I-j')

A mixture of (I-j) (100.0 g, 243.6 mmol, 1.0 equiv.), ethanolamine (200 mL), 2-methyl-tetrahydrofuran (2-MeTHF) (200 mL) and water (100 mL) is heated to about 70° C. The reaction mixture is stirred for about 4 h at about 70° C. 10% aq. NaCl solution (660 mL) and 2-MeTHF (300 mL) are added, and the reaction mixture is cooled to about 25-30° C. Phases are separated and organic phase is washed with 10% aq. NaCl solution (440 mL). About 300 mL of 2-MeTHF is then distilled out under vacuum at about 50° C., and toluene (500 mL) is added. The distillation is continued to remove about 400 mL of solvent. Toluene (500 mL) is then added and the mixture is heated to about 75-80° C. Resultant solution is filtered and filter is washed with 50 mL of hot (about 80° C.) toluene. Combined filtrates are cooled to about 40-50° C. and heptane (500 mL) is added slowly. The mixture is cooled to about 20-25° C. and stirred at this temperature for about 1 hour, and then it is filtered. The filter cake is washed with heptane. The product is dried at about 35° C. with a nitrogen flow for about 12 hours. The product is obtained as an off-white solid.

b) Preparation of (I-j') (Deprotection of (I-j)) (Route B)

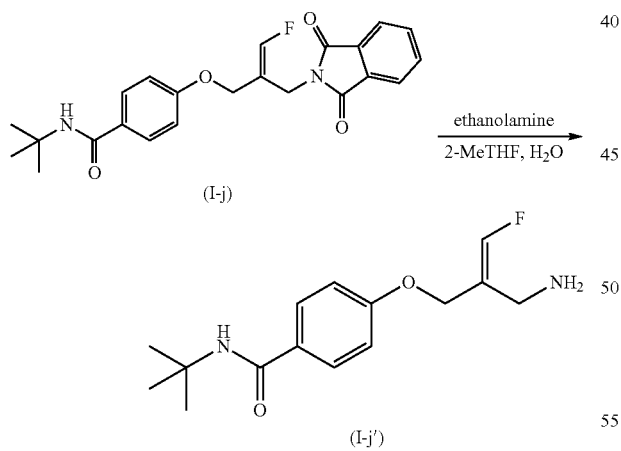

A mixture of (I-j) (10.0 g, 24.0 mmol, 1.0 equiv.), ethanolamine (20.2 g, 331.0 mmol, 13.6 equiv.), 2-MeTHF (20 mL) and water (10 mL) is heated to 68-70° C. After stirring the solution at this temperature for 3.5 h (IPC, conversion product >95%), water (40 mL) is added. The reaction mixture is cooled to 25-30° C. and MTBE (20 mL) and EtOAc (40 mL) are added. The resulting two phases are separated and water (60 mL) is added to the organic phase. The two phases are separated again and the organic phase is heated to 65° C. and solvent (60 mL) is distilled off under vacuum at this temperature. Toluene (50 mL) is added. The organic phase is heated to 65° C. and solvent (50 mL) is distilled off under vacuum at this temperature. Additional toluene (50 mL) is added, and the mixture is cooled to about 40-50° C. and heptane (50 mL) is added slowly. The mixture is cooled to about 20-25° C. and stirred at this temperature for about 1 hour, and then it is filtered. The filter cake is washed with heptane. The product is dried at about 35° C. with a nitrogen flow for about 12 hours. The product is obtained as an off-white solid.

(6) Procedure for the Formation of (I-k)

a) Preparation of Form I of (I-k) (Deprotection of (I-j) and Salt Formation) (Route A)

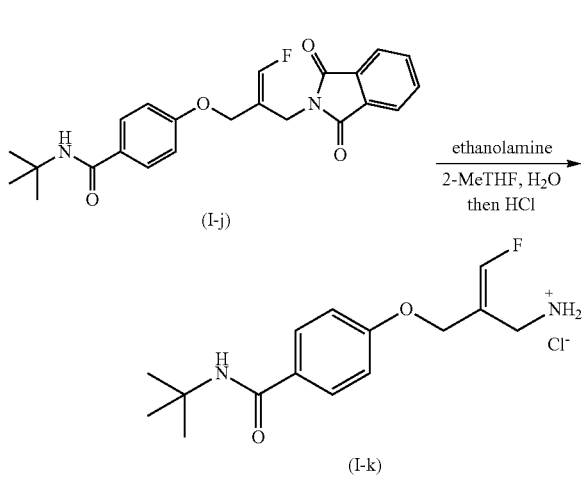

A mixture of (I-j) (100.0 g, 243.6 mmol, 1.0 equiv), ethanolamine (200 mL), 2-methyl-tetrahydrofuran (2-MeTHF) (200 mL) and water (100 mL) is heated to about 70° C. The reaction mixture is stirred for about 4 h at about 70° C. 10% aq. NaCl solution (660 mL) and 2-MeTHF (300 mL) are added, and the reaction mixture is cooled to about 25-30° C. Phases are separated and organic phase is washed with 10% aq. NaCl solution (440 mL). About 300 mL of 2-MeTHF is then distilled out under vacuum at about 50° C., and toluene (500 mL) is added. The distillation is continued to remove about 400 mL of solvent. Toluene (500 mL) is then added and the mixture is heated to about 75-80° C. Resultant solution is filtered and filter is washed with 50 mL of hot (about 80° C.) toluene. Combined filtrates are then diluted with isopropyl alcohol (250 mL) and heptane (300 mL), and solution is cooled to about 20-25° C. Solution of hydrogen chloride in isopropyl alcohol (5.64 M, 51.8 mL, 292.4 mmol, 1.2 equiv) is added at a rate to control the internal temperature at not more than 30° C. The mixture is stirred at about 20-25° C. for about 12 hours, and then it is filtered. The filter cake is washed with a mixture of heptane and isopropyl alcohol, 3:1 by volume (400 mL), followed by heptane (200 mL). The product is dried at about 50-65° C. under vacuum with a nitrogen flow for about 12 hours. The product (I-k) is obtained as off-white solid (69.2 g, 98.2 wt. % purity, 88% yield).

b) Preparation of Form I of (I-k) (Deprotection of (I-j) and Salt Formation) (Route B-1)

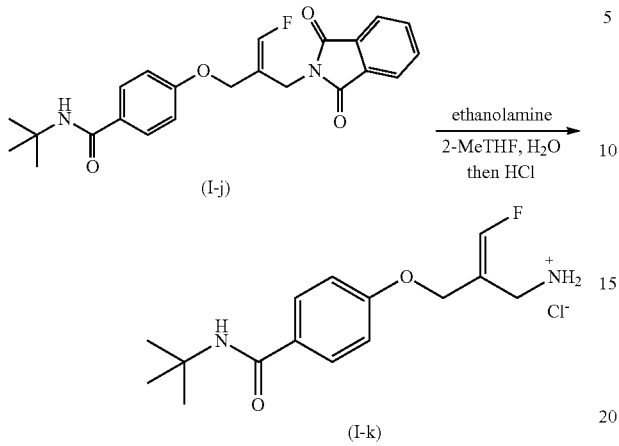

A mixture of (I-j) (10.0 g, 24.0 mmol, 1.0 equiv), ethanolamine (20.2 g, 331.0 mmol, 13.6 equiv), 2-methyl-tetrahydrofurane (2-MeTHF) (20 mL) and water (10 mL) is heated to 68-70° C. After stirring the solution at this temperature for 3.5 h [IPC, conversion product >95%], water (40 mL) is added. The reaction mixture is cooled to 25-30° C. and methyl tert-butyl ether (MTBE) (20 mL) and ethyl acetate (EtOAc) (40 mL) are added. The resulting two phases are separated and water (60 mL) is added to the organic phase. The two phases are separated again and the organic phase is heated to 65° C. and solvent (60 mL) is distilled off under vacuum at this temperature. EtOAc (50 mL) is added. The organic phase is heated to 65° C. and solvent (50 mL) is distilled off under vacuum at this temperature. EtOAc (25 mL) and isopropyl alcohol (20 mL) are added and the solution is heated to 68° C.

Isopropyl alcoholic HCl (5 mol/L, 5.31 g, 29.0 mmol, 1.2 equiv.) is added within 30 min at this temperature. Seed crystals are added and the resulting suspension is stirred for 25-35 min at 68° C. MTBE (50 mL) is added and the suspension is cooled to room temperature over a period of 25-35 min.

The product suspension is further stirred for 2 h at room temperature before it is filtered. The filter cake is washed with MTBE (40 mL) and the product is dried at about 60° C. under vacuum for about 5 h. The product (I-k) is obtained as an off-white crystalline solid (6.77 g, organic purity HPLC: 99.7 area %, yield: 87.7%).

c) Preparation of Form I of (I-k) (Deprotection of (I-j), Salt Formation and Recrystallization) (Route B-2)

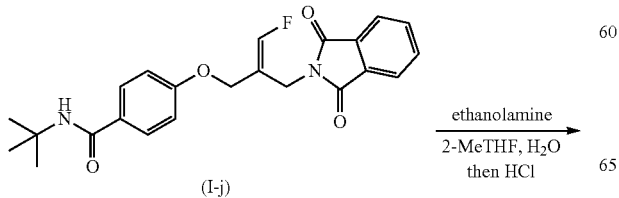

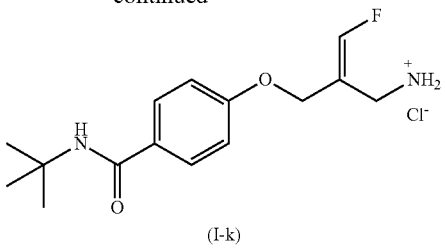

A mixture of (I-j) (200.0 g, 487.3 mmol, 1.0 equiv), ethanolamine (404.8 g, 662.7 mmol, 13.6 equiv), 2-methyl-tetrahydrofurane (2-MeTHF) (400 mL) and water (200 mL) is heated to 68-70° C. After stirring the solution at this temperature for 3.5 h [IPC, conversion product >95%], water (800 mL) is added. The reaction mixture is cooled to 40° C. and ethyl acetate (EtOAc) (1200 mL) is added. The resulting two phases are separated and water (1200 mL) is added to the organic phase. The two phases are separated again and the organic phase is heated to 65° C. and solvent (1070 mL) is distilled off under vacuum at this temperature. EtOAc (1000 mL) is added. The organic phase is heated to 65° C. and solvent (980 mL) is distilled off under vacuum at this temperature. EtOAc (500 mL) and isopropyl alcohol (500 mL) are added and the solution is heated to 68° C.

Isopropyl alcoholic HCl (5 mol/L, 106.3 g, 585 mmol, 1.2 equiv.) is added within 30 min at this temperature. Seed crystals are added and the resulting suspension is stirred for 25-35 min at 68° C. MTBE (1000 mL) is added and the suspension is cooled to room temperature over a period of 25-35 min.

The product suspension is further stirred for 16 h at room temperature before it is filtered. The filter cake is washed with MTBE (800 mL) and the product is dried at about 60° C. under vacuum for about 5 h. The product (I-k) is obtained as an off-white crystalline solid (134.9 g, organic purity HPLC: 99.6 area %, yield: 87.4%).

Recrystallization of Form I of (I-k)

Isopropyl Alcohol/Ethyl Acetate (EtOAc)/Methyl Tert-Butyl Ether (MTBE) Solvent System:

(I-k) (20 g, 63.1 mmol) is suspended in isopropyl alcohol (90 mL) and heated to 82° C. Ethyl acetate (EtOAc) (80 mL) is added to the solution under reflux conditions. After the addition of seed crystals at a temperature of 75-80° C. the mixture is stirred for 5 minutes. The resulting suspension is cooled to 56° C. over a period of 1 h. Methyl tert-butyl ether (MTBE) (70 mL) is added within 5 minutes at a temperature of >50° C. The product suspension is cooled to 0-5° C., stirred for 30 minutes and filtered. The filter cake is washed with MTBE (40 ml) and the product is dried at 75° C. for about 12 h under vacuum. The product (I-k) is obtained as an off-white crystalline solid (18.8 g, organic purity HPLC: 99.7 area %, yield: 93.9%).

or alternatively

Ethanol (EtOH)/Water/Ethyl Acetate (EtOAc) Solvent System:

(I-k) (11 g, 34.7 mmol) is suspended in ethanol (5.3 mL), H$_2$O (2.1 mL) and ethyl acetate (28.4 mL). The mixture is heated to 70° C. to dissolve (I-k). The resulting solution is cooled to ~55° C., seeded and aged 1 hour. Ethyl acetate (70.4 mL) is added over a period of 1 h at a temperature of ~55° C., aged 1 h and cooled to 15° C. in 1 h. The product suspension is stirred for 1 h and filtered. The filter cake is washed with EtOAc (24.7 mL) and the product is dried at 65° C. for about 12 h under vacuum. The product (I-k) is obtained as an off-white crystalline solid (10.1 g, organic purity HPLC: 99.9 area %, yield: 91.8%).

or alternatively

Isopropyl Alcohol/Water/Ethyl Acetate (EtOAc) Solvent System:

(I-k) (10 g, 31.5 mmol) is suspended in isopropyl alcohol (17.8 mL) and water (2 mL). The mixture is heated to 72° C. to dissolve (I-k). The resulting solution is cooled to 50° C., seeded and stirred 1 h. Ethyl acetate (118 mL) is added over a period of 1 h at a temperature of 50° C. and stirred for 1 h. The suspension is cooled to 10° C. over 2 h, stirred 2 h and filtered. The filter cake is washed with EtOAc (22.5 mL) and the product (I-k) is obtained as an off-white crystalline solid (8.8 g, organic purity HPLC: 99.5 area %, yield: 88%)

d) Preparation of Form II of (I-k)

(I-k), e.g. as obtained by the methods described herein, is dissolved in methanol at a concentration of about 50 mg/mL. The solution is heated to 60° C. and quickly transferred to a vacuum oven at 60° C. and dried over 15 minutes with dry air or dry nitrogen used as the vent gas to obtain Form II.

(7) XRPD Experiments a) Collection of XRPD Data

The X-ray powder diffraction profiles are acquired using a Bruker D8 Advance diffractometer in reflection mode equipped with a position sensitive detector using CuKα1 radiation (λ=1.54060 Å). For that purpose, the sample of (I-k) should be characterized by a purity above 99% as measured by HPLC, preferably the purity is above 99.5%, even more preferably above 99.7%, most preferably above 99.8%.

In order to allow for experimental error, the 2θ values described herein should be considered accurate to ±0.2 degrees 2θ, in particular ±0.1 degrees 2θ, even more specifically ±0.05 degrees 2θ. That is to say, when assessing whether a given sample of crystals of (I-k) is a crystalline form in accordance with the invention, a 2θ value which is experimentally observed for the sample should be considered identical with a characteristic value described herein if it falls within ±0.2 degrees 2θ, in particular ±0.1 degrees 2θ, even more specifically ±0.05 degrees 2θ of the characteristic value.

b) XRPD Data of Form I of (I-k) (Obtained Via Routes a, B-1 and B-2)

Characteristic XRPD peaks of Form I of (I-k) are summarized in the following table.

The corresponding XRPD pattern is depicted in FIG. 1.

| Peak | 2θ [°] |
|---|---|
| 1 | 3.82 |
| 2 | 7.63 |
| 3 | 11.46 |
| 4 | 13.55 |
| 5 | 15.29 |
| 6 | 16.03 |
| 7 | 16.38 |
| 8 | 17.15 |
| 9 | 17.80 |
| 10 | 18.73 |
| 11 | 19.02 |
| 12 | 19.35 |
| 13 | 19.69 |
| 14 | 20.80 |
| 15 | 21.65 |
| 16 | 22.20 |
| 17 | 22.64 |
| 18 | 23.03 |
| 19 | 23.63 |
| 20 | 24.58 |
| 21 | 25.11 |
| 22 | 25.83 |
| 23 | 26.21 |
| 24 | 26.93 |
| 25 | 27.30 |
| 26 | 27.79 |
| 27 | 28.93 |
| 28 | 29.24 |
| 29 | 31.03 |
| 30 | 31.52 |
| 31 | 32.28 |
| 32 | 32.94 |
| 33 | 33.60 |
| 34 | 34.27 | c) XRPD Data of Form II of (I-k)

Characteristic XRPD peaks of Form II of (I-k) are summarized in the following table.

Figure 2:
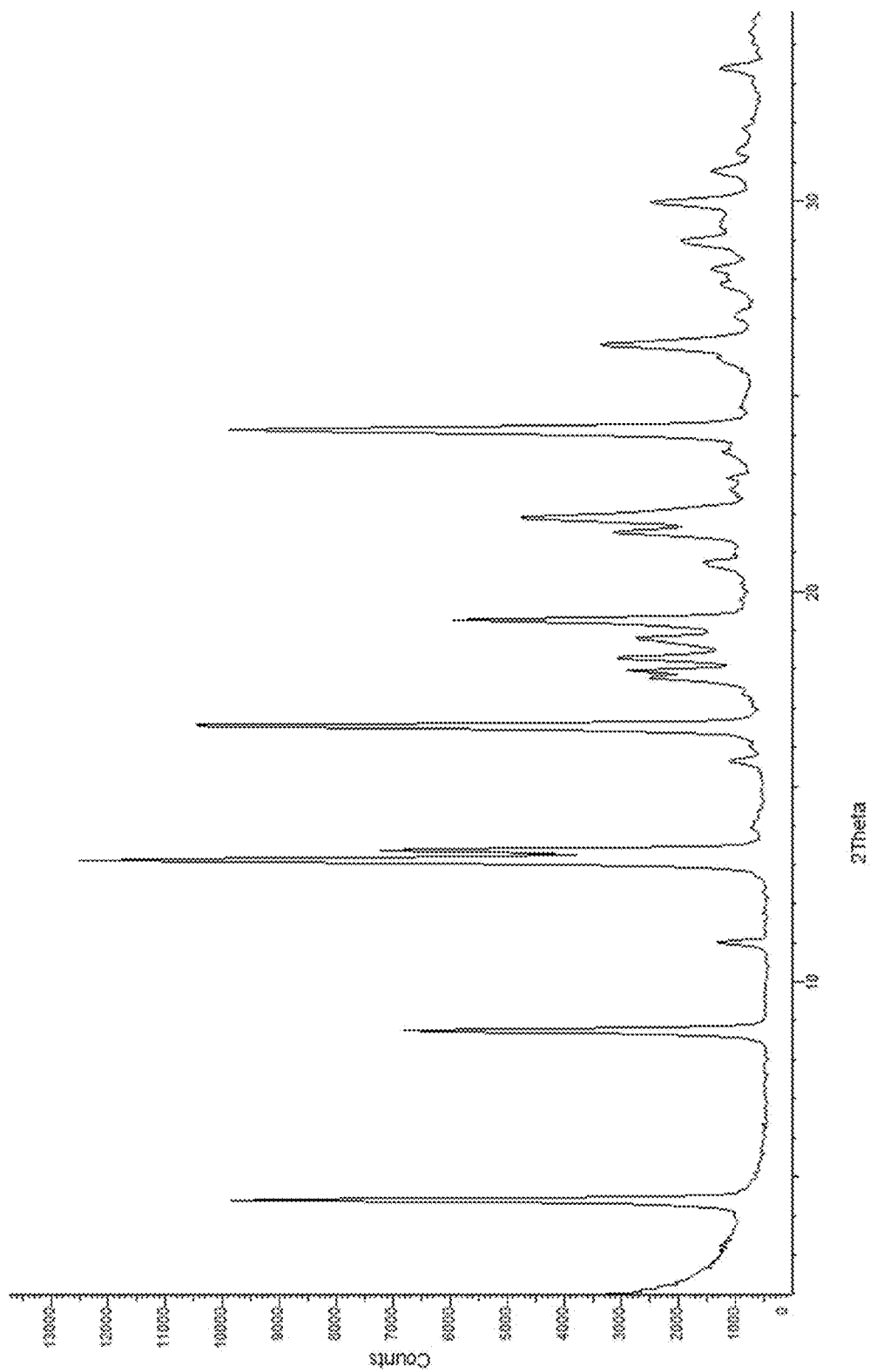
FIG. 2 shows the XRPD pattern of Form II of (I-k).

The corresponding XRPD pattern is depicted in FIG. 2.

| Peak | 2θ [°] |
|---|---|
| 1 | 4.42 |
| 2 | 8.72 |
| 3 | 11.00 |
| 4 | 13.11 |
| 5 | 13.35 |
| 6 | 15.64 |
| 7 | 16.58 |
| 8 | 17.82 |
| 9 | 17.94 |
| 10 | 18.31 |
| 11 | 18.81 |
| 12 | 19.26 |
| 13 | 20.75 |
| 14 | 21.53 |
| 15 | 21.88 |
| 16 | 22.92 |
| 17 | 24.13 |
| 18 | 26.30 |
| 19 | 27.05 |
| 20 | 27.90 |
| 21 | 28.27 |
| 22 | 28.99 |
| 23 | 29.98 |
| 24 | 30.78 |
| 25 | 31.85 |
| 26 | 33.43 |

(8) DSC Experiments

The melting point of Form I of (I-k) is determined to be 181° C.±5° C. by DSC as onset-temperature. DSC data is acquired using a TA Instruments Q2000 DSC from 25° C. to 225° C. at a heating rate of 10° C./min.

The corresponding DSC curve is depicted in FIG. 3.

(9) ssNMR Experiments a) Collection of $^{13}$C ssNMR Data ssNMR data is acquired on a Bruker Avance III NMR spectrometer (Bruker Biospin, Inc., Billerica, Mass.) at 9.4 T ($^1$H=400.46 MHz, $^{13}$C=100.70 MHz). Samples are packed in 4 mm O.D. zirconia rotors with Kel-F® drive tips. A Bruker model 4BL CP BB DVT probe is used for data acquisition and sample spinning about the magic-angle (54.74°). Sample spectrum acquisition uses a spinning rate of 12 kHz. A standard cross-polarization pulse sequence is used with a ramped Hartman-Hahn match pulse on the proton channel at ambient temperature and pressure. The pulse sequence uses a 2 ms contact pulse and a 5 s recycle delay. Two-pulse phase modulated (tppm) decoupling is also employed in the pulse sequence. No exponential line broadening is used prior to Fourier transformation of the free induction decay. Chemical shifts are referenced using the secondary standard of adamantane, with the upfield resonance being set to 29.5 ppm. The magic-angle is set using the $^{79}$Br signal from KBr powder at a spinning rate of 5 kHz.

In order to allow for experimental error, the chemical shifts described herein should be considered accurate to ±0.2 ppm, in particular ±0.1 ppm. That is to say, when assessing whether a given sample of (I-k) is a form in accordance with the invention, a chemical shift which is experimentally observed for the sample should be considered identical with a characteristic value described herein if it falls within ±0.2 ppm, in particular ±0.1 ppm of the characteristic value.

b) $^{13}$C ssNMR Data of Form I of (I-k)

The $^{13}$C NMR peaks of Form I of (I-k) are summarized in the following table (for the error range, see paragraph a)).

The corresponding $^{13}$C CPMAS ssNMR spectrum is depicted in FIG. 4.

| Peak | $^{13}$C Chemical Shift (ppm) |
|---|---|
| 1 | 167.9 |
| 2 | 162.5 |
| 3 | 161.1 |
| 4 | 156.6 |
| 5 | 154.0 |
| 6 | 151.4 |
| 7 | 149.0 |
| 8 | 148.4 |
| 9 | 131.3 |
| 10 | 130.1 |
| 11 | 129.2 |
| 12 | 128.3 |
| 13 | 119.3 |
| 14 | 113.1 |
| 15 | 112.0 |
| 16 | 110.9 |
| 17 | 67.4 |
| 18 | 65.2 |
| 19 | 51.9 |
| 20 | 35.2 |
| 21 | 29.9 |
| 22 | 29.0 | c) Collection of $^{19}$F ssNMR Data ssNMR data is acquired on a Bruker Avance III NMR spectrometer (Bruker Biospin, Inc., Billerica, Mass.) at 9.4 T. $^{19}$F ssNMR data is acquired using a 3.2 mm HFX DVT triple resonance probe. Samples are packed in 3.2 mm O.D. zirconia rotors with a Vespel® drive tip. The sample is spun about the magic angle (54.74°). Sample spectrum acquisition uses a spinning rate of 22 kHz. A single pulse with decoupling pulse sequence was used. Recycle delay is set at 15 s and 256 transients are acquired. Chemical shifts are referenced using the secondary standard of polyvinyldifluoride, with the main $CF_2$ resonance set to −92.1 ppm. Multiple spin populations are present due to the asymmetrical nature of the lineshape. Main resonance is at −115.1 ppm.

In order to allow for experimental error, the chemical shift described herein should be considered accurate to ±0.2 ppm, in particular ±0.1 ppm. That is to say, when assessing whether a given sample of (I-k) is a form in accordance with the invention, a chemical shift which is experimentally observed for the sample should be considered identical with a characteristic value described herein if it falls within ±0.2 ppm, in particular ±0.1 ppm of the characteristic value.

d) $^{19}$F ssNMR Data of Form I of (I-k)

The $^{19}$F chemical shift of Form I of (I-k) is determined as −115.1 ppm (for the error range, see paragraph c)).

Figure 5:
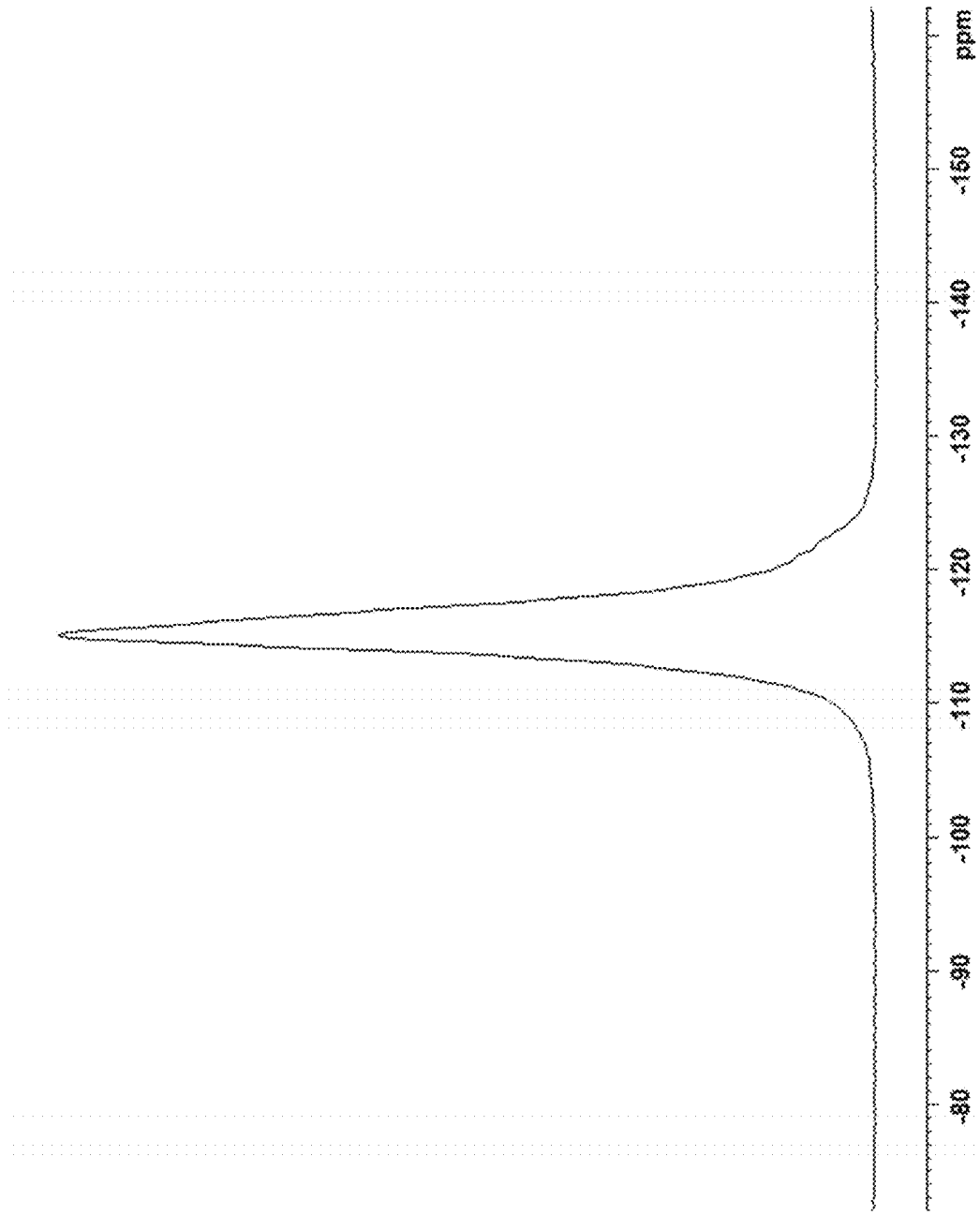
FIG. 5 shows the $^{19}$F ssNMR spectrum of Form I of (I-k).

The corresponding $^{19}$F ssNMR spectrum is depicted in FIG. 5.

The invention claimed is:

1. A method for the synthesis of a halo olefin of formula (I)

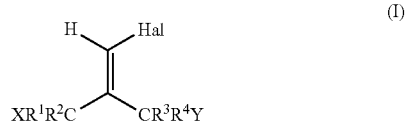

the method comprising the step (S1) of protodecarboxylation of an α-halo-acrylic acid derivative of formula (II)

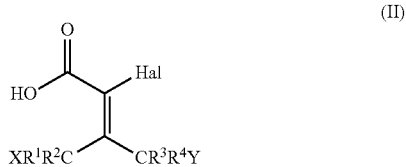

to provide the halo olefin of formula (I), wherein

Hal is selected from the group consisting of F, Cl, Br and I, and $R^1$, $R^2$, $R^3$ and $R^4$ are independently selected from the group $R^i$ consisting of H, halogen, CN, substituted or unsubstituted $C_{1-10}$-alkyl, substituted or unsubstituted $C_{3-10}$-cycloalkyl, substituted or unsubstituted $C_{2-10}$-alkenyl, substituted or unsubstituted $C_{2-10}$-alkynyl, substituted or unsubstituted aryl, substituted or unsubstituted aryl-$C_{1-6}$-alkylene-, substituted or unsubstituted heteroaryl and substituted or unsubstituted heteroaryl-$C_{1-6}$-alkylene-, and X and Y are independently selected from the groups consisting of $R^i$, $OR^X$, $SR^X$, $S(O)R^X$, $SO_2R^X$, $NR^{Y1}R^{Y2}$, $N(O)R^{Y1}R^{Y2}$, $PR^{Y1}R^{Y2}$ and $P(O)R^{Y1}R^{Y2}$, wherein $R^X$ is selected from the group of $R^i$, and wherein $R^{Y1}$ and $R^{Y2}$ are independently selected from the group consisting of $R^i$, $C(O)R^i$ and $C(O)OR^i$ or $R^{Y1}$ and $R^{Y2}$ are selected from the group $R^Y$ in which $R^{Y1}$ and $R^{Y2}$ are linked to form, together with N or P to which they are attached, substituted or unsubstituted heteroaryl or substituted or unsubstituted heterocyclyl, and $R^i$ is selected from the group R as defined hereinbefore;

or a salt thereof wherein (S1) is carried out in the presence of a catalytic amount of copper and/or silver.

2. The method according to claim 1, wherein copper and/or silver are employed in the form of oxides and/or salts selected from the group consisting of copper(I) oxide, copper(I) salts, silver(I) oxide and silver(I) salts.

3. The method according to claim 1, wherein Hal is F.

4. The method according to claim 1, wherein $R^1$, $R^2$, $R^3$ and $R^4$ are independently selected from the group consisting of H, halogen, CN and optionally partially or fully halogenated methyl, ethyl, n-propyl, iso-propyl, n-butyl, sec-butyl, iso-butyl, tert-butyl and cyclopropyl.

5. The method according to claim 1, wherein $R^i$ is selected from the group consisting of H, halogen, CN and optionally partially or fully halogenated methyl.

6. The method according to claim 1, wherein X is selected from the group consisting of $OR^X$, $SR^X$, $S(O)R^X$ and $SO_2R^X$,
wherein $R^X$ is selected from the group consisting of H, substituted or unsubstituted $C_{1-10}$-alkyl, substituted or unsubstituted $C_{3-10}$-cycloalkyl, substituted or unsubstituted $C_{2-10}$-alkenyl, substituted or unsubstituted $C_{2-10}$-alkynyl, substituted or unsubstituted aryl, substituted or unsubstituted aryl-$C_{1-6}$-alkylene-, substituted or unsubstituted heteroaryl and substituted or unsubstituted heteroaryl-$C_{1-6}$-alkylene-.

7. The method according to claim 1, wherein Y is selected from the group consisting of $NR^{Y1}R^{Y2}$, $PR^{Y1}R^{Y2}$ and $P(O)R^{Y1}R^{Y2}$,
wherein $R^{Y1}$ and $R^{Y2}$ are independently selected from the group consisting of
H, substituted or unsubstituted $C_{1-10}$-alkyl, substituted or unsubstituted $C_{3-10}$-cycloalkyl, substituted or unsubstituted $C_{2-10}$-alkenyl, substituted or unsubstituted aryl, substituted or unsubstituted aryl-$C_{1-6}$-alkylene-, substituted or unsubstituted $C_{1-10}$-alkyl-C(O)—, substituted or unsubstituted aryl-C(O)—, substituted or unsubstituted aryl-$C_{1-6}$-alkylene-C(O)—, substituted or unsubstituted $C_{1-10}$-alkyl-OC(O)—, substituted or unsubstituted aryl-OC(O)— and substituted or unsubstituted aryl-$C_{1-6}$-alkylene-OC(O)— or
$R^{Y1}$ and $R^{Y2}$ are selected from the group $R^Y$ in which $R^{Y1}$ and $R^{Y2}$ are linked to form, together with N or P to which they are attached, substituted or unsubstituted heteroaryl or substituted or unsubstituted heterocyclyl.

8. The method according to claim 1, wherein the compound of formula (II) is compound (II-g)

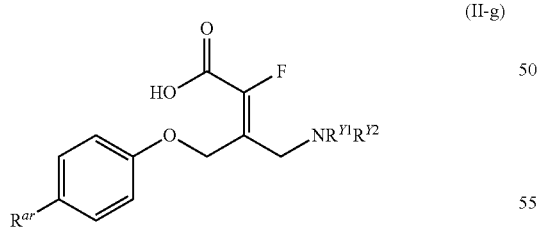

(II-g)

wherein $R^{ar}$ is selected from the group consisting of $C(O)NR^{N1}R^{N2}$ or $SO_2NR^{N1}R^{N2}$,
wherein $R^{N1}$ and $R^{N2}$ are independently selected from the group consisting of H, substituted or unsubstituted $C_{1-6}$-alkyl and substituted or unsubstituted $C_{3-7}$-cycloalkyl, and
wherein $R^{Y1}$ and $R^{Y2}$ are independently selected from the group consisting of H, substituted or unsubstituted acetyl, substituted or unsubstituted tert-butyloxycarbonyl, substituted or unsubstituted carboxybenzyl, substituted or unsubstituted fluorenylmethyloxycarbonyl, substituted or unsubstituted allyloxycarbonyl, substituted or unsubstituted tert-butyl, substituted or unsubstituted benzyl and substituted or unsubstituted phthaloyl or
$R^{Y1}$ and $R^{Y2}$ are selected from the group $R^Y$ in which $R^{Y1}$ and $R^{Y2}$ are linked to form, together with N to which they are attached, substituted or unsubstituted phthalimide or substituted or unsubstituted pyrrole; and
the compound of formula (I) is compound (I-g)

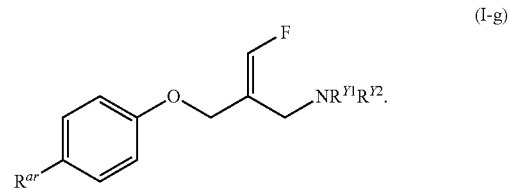

(I-g)

9. The method according to claim 8, wherein step (S1) comprises the deprotection of the compound of formula (I-g)

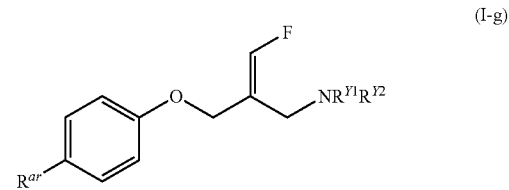

(I-g)

wherein $R^{ar}$ is selected from the group consisting of $C(O)NR^{N1}R^{N2}$ or $SO_2NR^{N1}R^{N2}$,
wherein $R^{N1}$ and $R^{N2}$ are independently selected from the group consisting of H, substituted or unsubstituted $C_{1-6}$-alkyl and substituted or unsubstituted $C_{3-7}$-cycloalkyl, and
wherein $R^{Y1}$ and $R^{Y2}$ are independently selected from the group consisting of H, substituted or unsubstituted acetyl, substituted or unsubstituted tert-butyloxycarbonyl, substituted or unsubstituted carboxybenzyl, substituted or unsubstituted fluorenylmethyloxycarbonyl, substituted or unsubstituted allyloxycarbonyl, substituted or unsubstituted tert-butyl, substituted or unsubstituted benzyl and substituted or unsubstituted phthaloyl or
$R^{Y1}$ and $R^{Y2}$ are selected from the group $R^Y$ in which $R^{Y1}$ and $R^{Y2}$ are linked to form, together with N to which they are attached, substituted or unsubstituted phthalimide or substituted or unsubstituted pyrrole;
to compound (I-g')

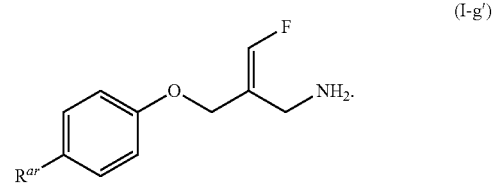

(I-g')

10. The method according to claim 1, wherein the compound of formula (II) is compound (II-j)

(II-j)

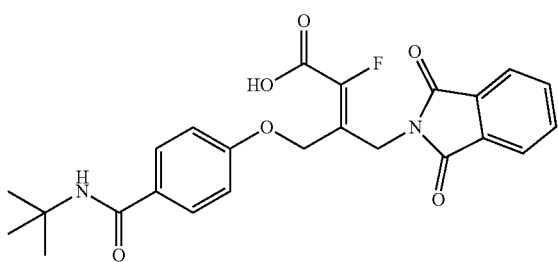

and
the compound of formula (I) is compound (I-j)

(I-j)

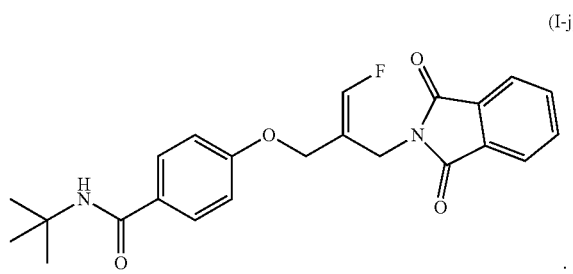

11. The method according to claim 1, further comprising the step (S2) for the formation of the α-halo-acrylic acid derivative of formula (II):

(II)

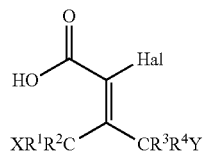

the step (S2) comprising reacting a ketone of formula (III)

(III)

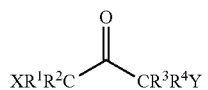

with a phosphonate of formula (IV)

(IV)

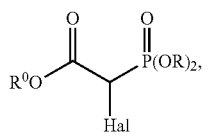

wherein
Hal is selected from the group consisting of F, Cl, Br and I,
$R^0$ is selected from the group consisting of H and $C_{1-6}$-alkyl, and R is selected from the group consisting of optionally partially or fully halogenated methyl, ethyl, n-propyl, iso-propyl, n-butyl, sec-butyl, iso-butyl and tert-butyl, phenyl, and
in the presence of at least one basic additive; and
in case $R^0$ is not H, saponification of the formed ester of formula (II')

(II')

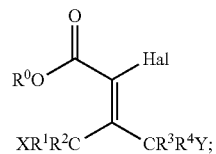

and
optional separation of the E and Z isomers of the compound of formula (II).

12. The method according to claim 11, wherein in step (S2) the compound of formula (III) is compound (III-g)

(III-g)

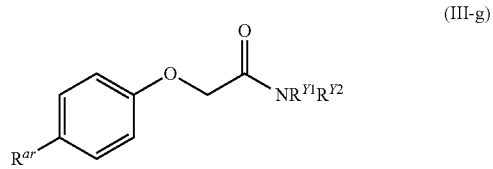

wherein $R^{ar}$ is selected from the group consisting of $C(O)NR^{N1}R^{N2}$ or $SO_2NR^{N1}R^{N2}$,
wherein $R^{N1}$ and $R^{N2}$ are independently selected from the group consisting of H, substituted or unsubstituted $C_{1-6}$-alkyl and substituted or unsubstituted $C_{3-7}$-cycloalkyl, and
wherein $R^{Y1}$ and $R^{Y2}$ are independently selected from the group consisting of H, substituted or unsubstituted acetyl, substituted or unsubstituted tert-butyloxycarbonyl, substituted or unsubstituted carboxybenzyl, substituted or unsubstituted fluorenylmethyloxycarbonyl, substituted or unsubstituted allyloxycarbonyl, substituted or unsubstituted tert-butyl, substituted or unsubstituted benzyl and substituted or unsubstituted phthaloyl or
$R^{Y1}$ and $R^{Y2}$ are selected from the group $R^Y$ in which $R^{Y1}$ and $R^{Y2}$ are linked to form, together with N to which they are attached, substituted or unsubstituted phthalimide or substituted or unsubstituted pyrrole,
and Hal in the phosphonate of formula (IV) is F,
and the compound of formula (II) is compound (II-g)

(II-g)

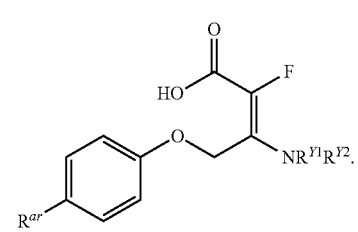

13. The method according to claim 11, wherein in step (S2) the compound of formula (III) is compound (III-j)

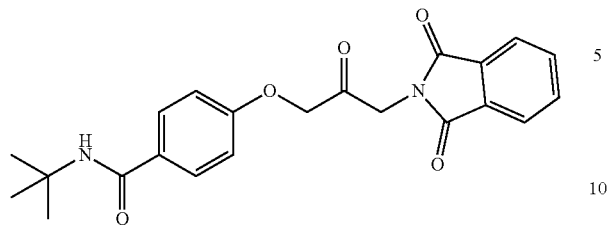
and the compound of formula (II) is compound (II-j)
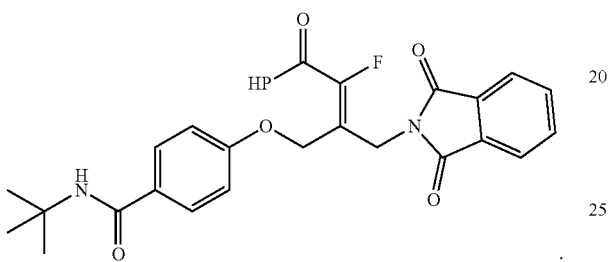
* * * * *